US010669221B2

(12) United States Patent
Vicente et al.

(10) Patent No.: US 10,669,221 B2
(45) Date of Patent: Jun. 2, 2020

(54) COMPOSITION OF CATALYSTS FOR CONVERSION OF ETHANOL TO N-BUTANOL AND HIGHER ALCOHOLS

(71) Applicant: ResCurve, LLC, Santa Barbara, CA (US)

(72) Inventors: Brian Christopher Vicente, Santa Barbara, CA (US); Peter K. Stoimenov, Goleta, CA (US)

(73) Assignee: ResCurve, LLC, Santa Barbara, CA (US)

( * ) Notice: Subject to any disclaimer, the term of this patent is extended or adjusted under 35 U.S.C. 154(b) by 0 days.

(21) Appl. No.: 15/753,064

(22) PCT Filed: Aug. 19, 2016

(86) PCT No.: PCT/US2016/047805
§ 371 (c)(1),
(2) Date: Feb. 15, 2018

(87) PCT Pub. No.: WO2017/031439
PCT Pub. Date: Feb. 23, 2017

(65) Prior Publication Data
US 2018/0370884 A1    Dec. 27, 2018

Related U.S. Application Data

(60) Provisional application No. 62/207,157, filed on Aug. 19, 2015.

(51) Int. Cl.
| | |
|---|---|
| *C07C 29/32* | (2006.01) |
| *B01J 21/00* | (2006.01) |
| *B01J 23/00* | (2006.01) |
| *B01J 23/44* | (2006.01) |
| *B01J 35/10* | (2006.01) |
| *B01J 35/00* | (2006.01) |
| *B01J 37/08* | (2006.01) |
| *B01J 37/16* | (2006.01) |
| *B01J 27/236* | (2006.01) |
| *B01J 21/10* | (2006.01) |
| *B01J 23/02* | (2006.01) |
| *B01J 23/72* | (2006.01) |

(52) U.S. Cl.
CPC ............ *C07C 29/32* (2013.01); *B01J 21/10* (2013.01); *B01J 23/02* (2013.01); *B01J 23/44* (2013.01); *B01J 23/72* (2013.01); *B01J 27/236* (2013.01); *B01J 35/002* (2013.01); *B01J 35/1014* (2013.01); *B01J 35/1038* (2013.01); *B01J 37/08* (2013.01); *B01J 37/16* (2013.01); *Y02P 20/127* (2015.11); *Y02P 20/582* (2015.11)

(58) Field of Classification Search
CPC .......... C07C 29/32; C07C 29/34; B01J 21/10; B01J 23/02; B01J 23/72
See application file for complete search history.

(56) References Cited

U.S. PATENT DOCUMENTS

| | | | |
|---|---|---|---|
| 1,992,480 | A | 2/1935 | Fuchs et al. |
| 2,525,829 | A | 10/1950 | Royer et al. |
| 2,645,667 | A | 7/1953 | Burgoyne |
| 3,714,236 | A | 1/1973 | Wright, Jr. et al. |
| 4,052,424 | A | 10/1977 | Vanderspurt |
| 4,220,803 | A | 9/1980 | Marcinkowsky et al. |
| 4,379,028 | A | 4/1983 | Berg et al. |
| 4,435,595 | A | 3/1984 | Agreda et al. |
| 4,440,946 | A | 4/1984 | Summerville et al. |
| 4,523,027 | A | 6/1985 | Kummer et al. |
| 4,569,726 | A | 2/1986 | Berg et al. |
| 4,645,570 | A | 2/1987 | Sridhar et al. |
| 4,825,013 | A | 4/1989 | Quarderer et al. |
| 4,996,007 | A | 2/1991 | Chao et al. |
| 5,194,675 | A | 3/1993 | Joerg et al. |
| 5,334,751 | A | 8/1994 | Lemanski et al. |
| 6,407,295 | B1 | 6/2002 | Kaizik et al. |
| 6,632,330 | B1 | 10/2003 | Colley et al. |
| 6,809,217 | B1 | 10/2004 | Colley et al. |
| 7,700,810 | B2 | 4/2010 | Kourtakis et al. |
| 7,700,811 | B2 | 4/2010 | Kourtakis et al. |
| 7,700,812 | B2 | 4/2010 | Kourtakis et al. |
| 7,700,813 | B2 | 4/2010 | Kourtakis et al. |
| 7,705,192 | B2 | 4/2010 | Kourtakis et al. |
| 7,745,672 | B2 | 6/2010 | Kourtakis et al. |
| 8,071,823 | B2 | 12/2011 | Ozer et al. |
| 8,080,684 | B2 | 12/2011 | Hassan et al. |
| 8,080,698 | B2 | 12/2011 | Eng |
| 8,304,587 | B2 | 11/2012 | Warner et al. |
| 8,318,989 | B2 | 11/2012 | Kourtakis et al. |
| 8,558,025 | B2 | 10/2013 | Gadewar |
| 8,562,921 | B2 | 10/2013 | Gadewar |
| 9,018,427 | B2 | 4/2015 | Gadewar et al. |
| 9,079,851 | B2 | 7/2015 | Gadewar et al. |

(Continued)

FOREIGN PATENT DOCUMENTS

| | | |
|---|---|---|
| BR | 9104652 A | 4/1993 |
| CN | 85105799 A | 11/1986 |

(Continued)

OTHER PUBLICATIONS

Foreign communication from a related counterpart application—International Preliminary Report on Patentability, PCT/US2014/068439, dated Jun. 16, 2016, 9 pages.

(Continued)

*Primary Examiner* — Sikarl A Witherspoon

(57) ABSTRACT

A method of producing a catalyst can include heating a hydrotalcite above a decomposition temperature, forming a decomposed hydrotalcite in response to the heating, combining the decomposed hydrotalcite with a metal salt to form a catalyst mixture, and heating the catalyst mixture to convert the metal salt to a metal oxide. The resulting metal oxide combined with the decomposed hydrotalcite forms the catalyst.

27 Claims, 11 Drawing Sheets

(56) References Cited

U.S. PATENT DOCUMENTS

| | | | |
|---|---|---|---|
| 2006/0178524 | A1 | 8/2006 | Zuber et al. |
| 2010/0160693 | A1 | 6/2010 | Kourtakis et al. |
| 2012/0035390 | A1 | 2/2012 | Gadewar |
| 2012/0165577 | A1 | 6/2012 | Fagan et al. |
| 2013/0197266 | A1 | 8/2013 | Gadewar et al. |
| 2014/0012037 | A1 | 1/2014 | Gadewar et al. |
| 2014/0171693 | A1 | 6/2014 | Zhang et al. |
| 2014/0235901 | A1* | 8/2014 | Gadewar ............... C07C 29/34 568/902.2 |

FOREIGN PATENT DOCUMENTS

| | | | |
|---|---|---|---|
| CN | 1255476 | A | 6/2000 |
| CN | 101065345 | A | 10/2007 |
| EP | 0101910 | A1 | 3/1984 |
| EP | 0151886 | A1 | 8/1985 |
| EP | 0201105 | A1 | 11/1986 |
| EP | 0331021 | A1 | 9/1989 |
| EP | 1829851 | A1 | 9/2007 |
| EP | 2679303 | A1 | 1/2014 |
| EP | 2679304 | A1 | 1/2014 |
| EP | 3219385 | A1 | 9/2017 |
| FR | 2743060 | A1 | 7/1997 |
| GB | 287846 | | 4/1929 |
| GB | 312345 | | 8/1930 |
| GB | 470773 | | 8/1937 |
| JP | 59025334 | A | 2/1984 |
| JP | H0753676 | A | 10/1988 |
| JP | 5186392 | A | 7/1993 |
| JP | 2009220105 | A | 10/2009 |
| SU | 362814 | A1 | 12/1972 |
| WO | 2011131609 | A2 | 10/2011 |
| WO | 2012004572 | A1 | 1/2012 |
| WO | 2013055334 | A1 | 4/2013 |
| WO | 2013116492 | A1 | 8/2013 |
| WO | 2014130465 | A1 | 8/2014 |
| WO | 2015085002 | A1 | 6/2015 |
| WO | 2016075353 | A1 | 5/2016 |
| WO | 2017031439 | A1 | 2/2017 |

OTHER PUBLICATIONS

Foreign communication from a related counterpart application—International Preliminary Report on Patentability, PCT/US2016/047805, dated Mar. 1, 2018, 18 pages.

Foreign communication from a related counterpart application—International Search Report and Written Opinion, PCT/US2014/068439, dated Feb. 26, 2015, 12 pages.

Foreign communication from a related counterpart application—International Search Report and Written Opinion, PCT/US2016/047805, dated Nov. 28, 2016, 20 pages.

Galvita, Vladimir et al., "Ethane dehydrogenation on Pt/Mg(Al)O and PtSn/Mg(Al)O catalysts," Journal of Catalysis, 2010, vol. 271, No. 2, pp. 209-219.

Gines, Marcelo J. L., et al., "Bifunctional Condensation Reactions of Alcohols on Basic Oxides Modified by Copper and Potassium," Journal of Catalysis, 1998, pp. 155-172, vol. 176, Academic Press.

Hui, Sun, Multifunctional and multi-staged reactors for liquid fuel generation from renewable feedstocks, 2012, PhD Thesis.

Inui, Kanichiro, et al., "Direct synthesis of ethyl acetate from ethanol carried out under pressure," Journal of Catalysis, 2002, pp. 207-215, vol. 212, Elsevier Science.

Inui, Kanichiro, et al., "Effective formation of ethyl acetate from ethanol over Cu—Zn—Zr—Al—O catalyst," Journal of Molecular Catalysis A: Chemical, 2004, pp. 147-156, vol. 216, Elsevier B.V.

Le Valant, Anthony et al., "Hydrogen production from raw bioethanol over Rh/MgAl2O4 catalyst impact of impurities: Heavy alcohol, aldehyde, ester, acid and amine," Catalysis Today, 2008, vol. 138, Nos. 3-4, pp. 169-174.

Santacesaria, E., et al., "Ethanol dehydrogenation to ethyl acetate by using copper and copper chromite catalysts," Chemical Engineering Journal, 2012, pp. 209-220, vol. 179, Elsevier B.V.

Sharma, M. M., et al., "Industrial Applications of Reactive Distillation, Part I," 2002, 28 pages, Wiley-VHC Verlag GmbH & Co. KGaA.

Smith, Michael B., "March's advanced organic chemistry: reactions, mechanisms, and structure," 7th edition, 2013, 8 pages of cover, publishing information, and contents, John Wiley & Sons, Inc.

Takeshita, Kenji, et al., "Reduced copper catalyzed conversion of primary alcohols into esters and ketones," Bulletin of the Chemical Society of Japan, Sep. 1978, pp. 2622-2627, vol. 51, No. 9.

Tsai, Reui-Chiang, et al., "Design and control of the side reactor configuration for production of ethyl acetate," Ind. Eng. Chem. Res., 2008, pp. 9472-9484, vol. 47, No. 23, American Chemical Society.

Tsuchida, Takashi, et al., "Reaction of ethanol over hydroxyapatite affected by Ca/P ratio of catalyst," Journal of Catalysis, 2008, pp. 183-189, vol. 259, Elsevier, Inc.

Vogel, Arthur Israel, "Vogel's textbook of practical organic chemistry," 5th edition, revised by Brian S. Furniss, et al., 1989, 15 pages of cover, publishing information, and contents, John Wiley & Sons, Inc.

Xia, Ke et al. "Analysis of the catalytic activity induction and deactivation of PtIn/Mg(Al)O catalysts for propane dehydrogenation reaction," RSC Advances, Jul. 15, 2015 (e-pub), vol. 5, No. 79, pp. 64689-64695.

Yang, Ke Wu, et al., "One-step synthesis of n-Butanol from ethanol condensation over alumina-supported metal catalysts," Chinese Chemical Letters, 2004, pp. 1497-1500, vol. 15, No. 12.

Foreign communication from a related application—Extended European Search Report of Application No. 14754744.2 dated Nov. 21, 2016, 10 pages.

Foreign communication from a related application—First Office Action, Chinese Application No. 201480009376.7 dated Jul. 29, 2016, with English translation, 13 pages.

Foreign communication from a related counterpart application—International Search Report and Written Opinion, PCT/US2014/016957, dated Jun. 27, 2014, 9 pages.

Foreign communication from a related counterpart application—International Search Report and Written Opinion, PCT/US2013/024104, dated May 30, 2013, 12 pages.

Foreign communication from a related counterpart application—International Search Report and Written Opinion, PCT/US2011/056015, dated May 24, 2012, 8 pages.

Filing receipt and specification for international application entitled "Ethyl acetate production," filed Oct. 20, 2010 as international application No. PCT/US2010/002806.

Filing receipt and specification for provisional patent application entitled "Ethyl acetate production," by Sagar B. Gadewar, filed Oct. 20, 2009 as U.S. Appl. No. 61/253,349.

Filing receipt and specification for provisional patent application entitled "Production of butanols and ethyl acetate," by Sagar B. Gadewar, et al., filed Feb. 19, 2013 as U.S. Appl. No. 61/766,484.

Filing receipt and specification for provisional patent application entitled "Production of ethyl acetate and butyl acetates from ethanol," by Sagar B. Gadewar, et al., filed Dec. 4, 2013 as U.S. Appl. No. 61/911,832.

Foreign communication from a related counterpart application—Search Report, European Application No. 11873809.5 dated Apr. 15, 2015, 7 pages.

Foreign communication from a related counterpart application—International Search Report and Written Opinion, PCT/US2014/053894, dated Oct. 31, 2014, 9 pages.

Foreign communication from a related counterpart application—International Preliminary Report on Patentability, PCT/US2011/056015, dated Apr. 15, 2014, 6 pages.

Foreign communication from a related counterpart application—International Preliminary Report on Patentability, PCT/US2013/024104, dated Aug. 5, 2014, 9 pages.

Office Action of U.S. Appl. No. 15/101,251 dated Oct. 18, 2017, 15 pages.

Yamamoto, Nobuyuki, et al., "The Direct Conversion of Ethanol to Ethyl and Methyl Acetates Catalyzed by Iridium Complex," Chemistry Letters, 2009, pp. 1106-1107, vol. 38, No. 11.

(56) References Cited

OTHER PUBLICATIONS

Marcu, Ioan-Cezar, et al., "Catalytic valorization of bioethanol over Cu—Mg-Ak mixed oxide catalysts," Catalysis Today, 2009, pp. 231-238, vol. 147.

Sushkevich, Vitaly L., et al., "Mechanistic Study of Ethanol Dehydrogenation over Silica Supported Silver," ChemCatChem, 2013, pp. 2367-2373, vol. 5.

Foreign communication from a related application—Extended European Search Report, EP Application No. 16837918.8, dated Apr. 17, 2019, 7 pages.

* cited by examiner

COMPOSITION OF CATALYSTS FOR CONVERSION OF ETHANOL TO N-BUTANOL AND HIGHER ALCOHOLS

CROSS-REFERENCE TO RELATED APPLICATIONS

This application is a filing under 35 U.S.C. 371 of International Application No. PCT/US2016/047805 filed Aug. 19, 2016 and entitled "Composition of Catalysts for Conversion of Ethanol to N-Butanol and Higher Alcohols," which claims priority to U.S. Provisional Patent Application No. 62/207,157 filed on Aug. 19, 2015 and entitled "Composition of Catalysts for Conversion of Ethanol to N-Butanol and Higher Alcohols," which applications are incorporated by reference herein in their entirety.

BACKGROUND

N-Butanol and ethyl acetate are commercially significant organic compounds having use in a wide variety of applications and which are produced in quantities exceeding 1 million tons per year. N-Butanol can be produced from several different reactions. The most common method for making n-butanol is hydroformylation. Propylene reacts with syngas over cobalt or rhodium catalysts at high pressures to produce an aldehyde (butyraldehyde), which is then hydrogenated over a nickel catalyst to give the alcohol. The drawbacks of such a process include the high energy costs associated with the generation of syngas, the use of a potentially non-renewable feedstocks (propylene and syngas are typically sourced from petroleum and natural gas, respectively), and the complexity of the process which requires multiple reactors and, typically, homogenous hydroformylation catalysts.

N-Butanol can also be produced from an aldol condensation reaction followed by hydrogenation. This method converts acetaldehyde to butanols, although the high toxicity and limited availability of acetaldehyde make such a process unattractive. Some processes, for example U.S. Pat. Nos. 1,992,480 and 8,071,823 both of which are incorporated herein by reference in their entirety, utilize a gas phase reaction to provide butanol.

Direct fermentation of sugars is another process for production of n-butanol. As a bioprocess this method suffers from long process times and large separation requirements in addition to the need for specialized microbes necessary to make butanol directly from sugars.

SUMMARY

In an embodiment, a method of producing a catalyst comprises heating a hydrotalcite above a decomposition temperature, forming a decomposed hydrotalcite in response to the heating, combining the decomposed hydrotalcite with a metal salt to form a catalyst mixture, and heating the catalyst mixture to convert the metal salt to a metal oxide. The resulting metal oxide combined with the decomposed hydrotalcite forms the catalyst.

In an embodiment, a catalyst comprises a first material having a formula:

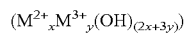

and one or more second materials. The $M^{2+}$ ions comprise one or more of Mg, Ni, Pt, Pd, Zn, Co, Fe, or Cu, and the $M^{3+}$ ions comprise at least one of Al, Fe, or Cr. The value of x is in the range of from 2 to 7, and the value of y is in the range of from 1.5 to 2.5. The one or more second materials can include at least one of Pt, Pd, Cu, $Cr_2O_3$, $CuCr_2O_5$, Ni, Fe, Ru, Rh, Ir, Os, or Co.

In an embodiment, a catalyst comprises a first material having a formula:

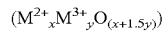

and one or more second materials. The $M^{2+}$ ions comprise one or more of Mg, Ni, Pt, Pd, Zn, Co, Fe, or Cu, and the $M^{3+}$ ions comprise at least one of Al, Fe, or Cr. The value of x is in the range of from 0.5 to 1.5, and the value of y is in the range of from 1.5 to 4. The one or more second materials comprising at least one of Pt, Pd, Cu, Cr2O3, Ni, Fe, Ru, Rh, Ir, or Co.

In an embodiment, a method for producing a higher alcohol comprises contacting a reactant comprising ethanol with a catalyst at a reaction temperature and pressure sufficient to produce a reaction product. The catalyst comprises a decomposed hydrotalcite mixed with one or more metal oxides, and the reaction product comprises a higher alcohol.

These and other features will be more clearly understood from the following detailed description taken in conjunction with the accompanying drawings and claims.

BRIEF DESCRIPTION OF THE DRAWINGS

For a more complete understanding of the present disclosure and the advantages thereof, reference is now made to the following brief description, taken in connection with the accompanying drawings and detailed description.

DETAILED DESCRIPTION

Figure 1:
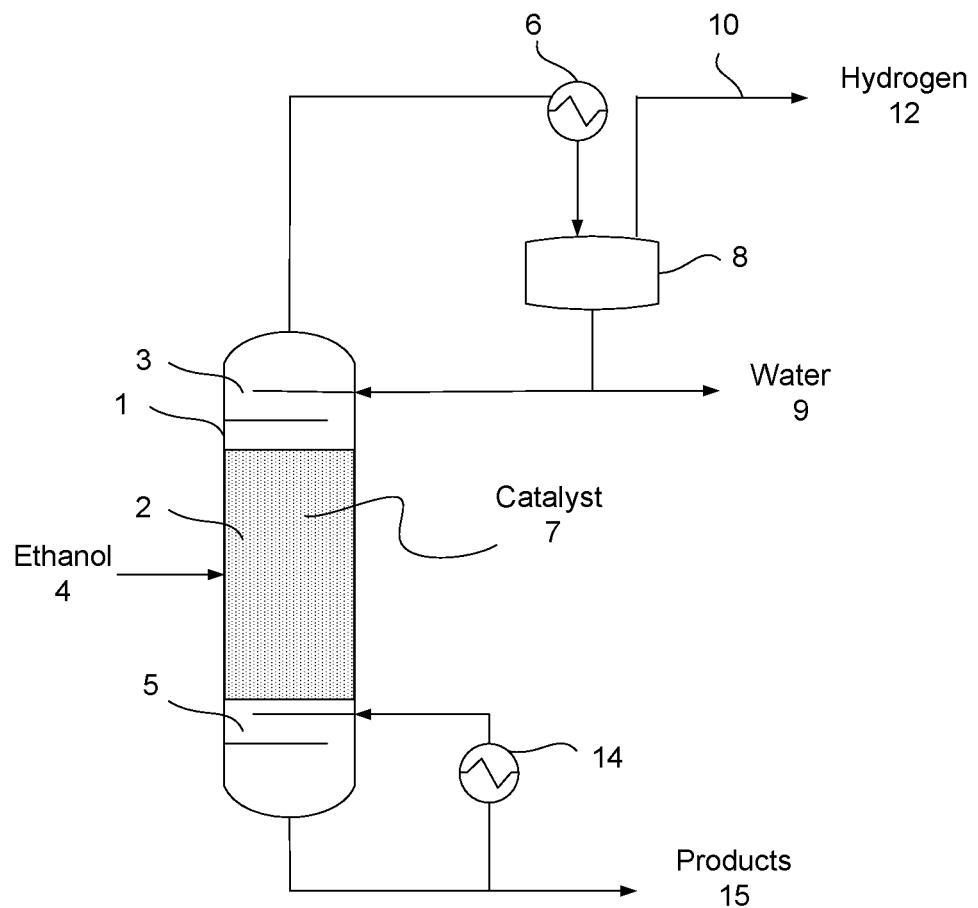
FIG. 1 shows a simplified schematic of a reactive distillation system according to an embodiment.

The present application is directed to a variety of new catalysts capable of catalytically converting inexpensive alcohol feedstock such as bio-renewable ethanol to higher value, larger carbon number, primary alcohols, preferably n-butanol and higher alcohols (e.g., higher homolog members in the $C_6$-$C_{13}$ carbon range of saturated alcohols) along with methods and processes for the creation of the catalysts. These alcohols can have multiple high volume applications as plasticizers, surfactants, co-surfactants and property improving additives. The alcohols can be further converted to other desirable, high value chemical products such as esters or olefins which also have a multitude of applications.

As used herein, higher alcohols refer to saturated alcohols have a higher molecular weight than the alcohol forming the reactant in the formation process. In some embodiments, the higher alcohols can include $C_4$-$C_{20}$ alcohols, or even higher alcohols. This process is beneficial as it provides an improved commercial method of upgrading ethanol to higher alcohols such as n-butanol, which are more valuable products. This improved commercial process may be used where there is a supply and/or a surplus supply of ethanol. Further, this process reduces and/or eliminates the need for separate syngas and n-butyraldehyde plants to provide the precursors for the butanol production process, and reduces and/or eliminates reliance on syngas as a precursor, which is expensive to produce and requires a non-renewable resource when obtained from petroleum and natural gas. This process also reduces and/or eliminates the need for a separate acetaldehyde plant to provide the precursors for the butanol production process, and reduces and/or eliminates reliance on highly toxic acetaldehyde.

Although there is some literature on catalytic conversion of ethanol to n-butanol, the process is not practiced commercially as described. There is a similar process described in literature and known for some time where the reaction is performed in a liquid phase in a batch reactor in the presence of catalyst (e.g., using the Guerbet reaction). The process is not practiced commercially due to loss of catalyst due to side reactions and the formation of many undesirable products.

Currently, n-butanol and higher alcohols are made by hydroformylation of olefins such as ethylene, propylene and butylene followed by hydrogenation. Disadvantages to the current technology include the generation of significant quantities of branched alcohols, the use of petroleum derived starting materials, and generally low selectivity.

The catalysts that are described herein are prepared in a way that is different from the preparations described in literature. The difference in their preparation may create a different structure that enables a higher performance in comparison with similarly prepared catalysts.

The mechanism for the conversion of ethanol to n-butanol (and/or higher alcohols) is a multi-step reaction that requires two different catalytic functions. The catalysts for this process must perform both alcohol dehydrogenation/aldehyde hydrogenation and aldol condensation.

Dehydrogenation: $C_2H_5OH \leftrightarrows CH_3CHO+H_2$ (dehydrogenation/hydrogenation catalyst component)      (Eq. 1)

Aldol condensation: $CH_3CHO+CH_3CHO \rightarrow CH_3CH(OH)CH_2CHO$ (aldol catalyst component)      (Eq. 2)

Dehydration: $CH_3CH(OH)CH_2CHO \rightarrow CH_3CH=CHCHO+H_2O$ (spontaneous, no catalyst)      (Eq. 3)

Hydrogenation: $CH_3CH=CHCHO+2H_2 \leftrightarrows CH_3CH_2CH_2CHO$ (dehydrogenation/hydrogenation catalyst component)      (Eq. 4)

The overall reaction is a dehydration:

$$2C_2H_5OH \rightarrow n\text{-}C_4H_9OH+H_2O$$

It is worth nothing that due to the relatively complicated mechanism, simple dehydration catalyst, such as alumina and silica do not form any n-butanol when ethanol is passed over them. While not intending to be limited by theory, when higher alcohols are generated, the chain elongation may occur from further aldol condensation of the unsaturated aldehyde (Eq. 3) to form linear primary alcohols:

$CH_3CH=CHCHO+CH_3CHO \rightarrow CH_3CH=CHCH=CHCHO+H_2O$      (Eq. 5)

$CH_3CH=CHCH=CHCHO+3H_2 \rightarrow CH_3CH_2CH_2CH_2CH_2OH$      (Eq. 6)

or through the reaction of butyraldehyde with acetaldehyde to form the corresponding branched hexanol (2-ethylbutanol):

$CH_3CH_2CH_2CHO+CH_3CHO \rightarrow CH_3CH_2CHCH_2C(CH_3CH=)CHO+H_2O$      (Eq. 7)

$CH_3CH_2CHCH_2C(CH_3CH=)CHO+2H_2 \rightarrow CH_3CH_2CHCH_2C(CH_3CH_2)CH_2OH$      (Eq. 8)

In some embodiments, the catalyst described here can have the two components: 1) hydrogenation/dehydrogenation and 2) aldol condensation.

Various elements can act as the hydrogenation/dehydrogenation component. In an embodiment, the catalyst can comprise Pt, Cu, $Cr_2O_3$, Ni, Fe, Ru, Rh, Co, $Cu_2Cr_2O_5$ either standalone or dispersed on various supports. In some embodiments, the catalyst can comprise Pd and/or Cu either standalone or dispersed on various supports. Supports may be important in hydrogenation catalysis as they may potentiate the activity or selectively reduce the activity of the hydrogenation catalyst.

In an embodiment, a thermally decomposed hydrotalcite or a thermally decomposed hydrotalcite pretreated with metal salts to increase the basicity can be used for the aldol condensation coupling catalyst component. Hydrotalcite has a general formula:

$$(M^{2+}_{1-x}M^{3+}_x(OH)_2)(A^{n-}_{x/n}) \cdot yH_2O$$

The $M^{2+}$ ions can be a variety of divalent cations (e.g., Mg, Ni, Pt, Pd, Zn, Co, Fe, Cu) and the $M^{3+}$ ions can be trivalent Al, Fe or Cr. Hydrotalcite is a mineral that has a peculiar lamellar structure where a magnesium-aluminum mixed oxide forms a backbone of a structure with layers of exchangeable counter anions between the metal oxide sheets. The hydrotalcite used for preparation of the catalyst can be obtained commercially as a synthetic hydrotalcite, although naturally occurring hydrotalcite can have substantially the same catalytic activity. The commercial hydrotalcite generally has a mixture of carbonate and hydroxide anions as counter ions, although these anions can be changed to improve or optimize reactivity.

An alternative to hydrotalcite is hydrocalumite, which has a different range of composition yet has a similar double hydroxide layer structure (e.g. $Ca_2Al(OH)_6[Cl_{1-x}(OH)_x] \cdot 3(H_2O)$). Hydrocalumite used for catalyst preparation would be used in the same fashion as the hydrotalcite except higher temperatures will be used for its decomposition (400° C.-1000° C.). While portions of the present application describe catalysts prepared with hydrotalcite, both natural or synthetic hydrocalumite can be used in the catalysts described herein in place of hydrotalcite or in combination with hydrotalcite.

The catalyst of the present description can be prepared using several processes as described below.

1. Preparation of Aldol Condensation Component.

Upon heating, the hydrotalcite decomposes irreversibly above about 350° C. This decomposition is accompanied by loss of crystallinity and the organized lamellar layer structure collapses, generating a very intimate magnesium aluminum oxide mixture. Subsequently, the mixture may crystallize in new phases such as meixnerite ($Mg_6Al_2(OH)_{18} \cdot 4H_2O$). The resulting magnesium aluminum oxide mixture is referred to as a decomposed hydrotalcite, which can be treated in various ways in subsequent processes, including the addition of the hydrogenation/dehydrogenation component. The degree of decomposition, crystallinity loss and structural changes varies with temperature and duration of the heat treatment. In some embodiments, the range of decomposition temperatures can be between about 350° C. and about 800° C., between about 450° C. and about 500° C., or alternatively at a temperature of about 475° C.

2. Preparation of Aldol Condensation Component.

Hydrotalcite can be mixed with a metal salt such as alkaline earth or alkaline metal nitrate, chloride, acetate, formate or any other soluble salt of the desired metal. Most preferable are organic acid salts as they decompose quickly and completely to form the corresponding metal oxides which may react further with the thermally decomposed hydrotalcite product. The salts can be delivered as relatively concentrated solutions added to an aqueous or ethanol/water suspension of the thermally decomposed hydrotalcite or hydrotalcite (e.g., as a slurry) to facilitate the wetting of the hydrotalcite particles (synthetic hydrotalcite is a hydrophobic substance). The slurry can be heated to about 105° C. until dry followed by annealing at elevated temperature (e.g., between about 300° C. and about 500° C.). The heating generates a thermally decomposed hydrotalcite containing a higher amount (in relation to stoichiometric content in the hydrotalcite) of strongly basic metal oxide such as magnesium or calcium oxide.

In an embodiment, the decomposed hydrotalcite with or without the metal salt treatment can comprise a variety of structures including a meixnerite ($Mg_6Al_2(OH)_{18} \cdot 4H_2O$) phase.

The decomposed hydrotalcite with or without the metal salt treatment is treated further with an aqueous solution comprising a desired hydrogenation/dehydrogenation component. For example, the decomposed hydrotalcite with or without the metal salt treatment can be further treated with Pd, Cu, or another of the desired hydrogenation/dehydrogenation metal salts as precursors listed herein. In an embodiment, the decomposed hydrotalcite can be treated by incipient wetting method or by drying of a slurry of the decomposed hydrotalcite material in the corresponding metal salt solution. After drying at a temperature between about 85° C. and about 105° C., the material can either be heated to high temperature (to decompose the metal salt to corresponding metal (e.g. Pd, Pt) or metal oxides ($Fe_2O_3$ and CuO)). The heating can be done in air, in an inert atmosphere (e.g. nitrogen) or in a reducing atmosphere (e.g. in the presence of hydrogen). The same conversion of metal salt to metal or metal oxide can be achieved by chemical means without heating in air such as by reduction with gaseous hydrogen, reduction with an aqueous or organic solution of reactants such as hydrazine, hydroxylamine, formaldehyde, ascorbic acid (vitamin C), sodium dithionite, sodium borohydride or other common reducing agents.

In an embodiment of the preparation of the catalyst material as described above, the process can begin with commercially available hydrotalcite. The hydrotalcite can be decomposed prior to loading the dehydrogenation/hydrogenation component. The dehydrogenation/hydrogenation component can then be loaded on an already decomposed hydrotalcite, and thus, the hydrogenation catalyst component can be generated on the surface of the thermally decomposed hydrotalcite. The ratio of hydrogenation catalyst component to hydrotalcite can be varied at will and there are no limitations as in the end the two catalyst components generate a physical mixture of metal particles (e.g. Pd) loaded on the surface of the mixture of intimate magnesium and aluminum oxides generated from the decomposition of the hydrotalcite. In some embodiments, the catalyst material can comprise Pd having a loading between about 0.01 wt % and about 5 wt. % of the catalyst material.

The catalyst prepared according to the present disclosure is distinct from a catalyst that is prepared by first loading the dehydrogenation/hydrogenation metal component into the hydrotalcite mineral structure (e.g., the Pd(II) or Cu(II)). A catalyst having the metal component first loaded into the hydrotalcite can be created by loading the metal component (e.g. Pd(II) introduced as $Pd(NO_3)_2$) into the crystal structure of the hydrotalcite. The metal ions (e.g., Pd(II) ions) can then exchange with the $M^{2+}$ component isomorphically in the Mg(II) sites in the hydrotalcite structure. The catalyst that catalyzes the conversion of ethanol to n-butanol with the M(II) replacing the Mg(II)) is then generated upon thermal decomposition of the exchanged structure. The use of a process that first loads the dehydrogenation/hydrogenation component into the mineral catalyst limits the amount of the components that may be introduced before the hydrotalcite structure becomes difficult, if not impossible, to form.

Thus the preparation process described herein differs in that the hydrogenation component is added after the hydrotalcite structure has already collapsed (e.g., due to thermal decomposition, etc.), which is expected to provide a different dispersion of the two components within the catalyst and thereby improve the performance of the catalyst. While not intending to be limited by theory, it is expected that decomposing the hydrotalcite first may generate a coarser dispersion of the components. While this can result in a decreased performance in some instances, it has been unexpectedly found to improve the conversion to n-butanol in the current applications. Further, the inclusion of the dehydrogenation/hydrogenation component after the hydrotalcite is decomposed may provide for a broader range of loadings that can exceed the stoichiometric limit present in an ion exchanged hydrotalcite. As noted above, the catalyst material can also use hydrocalumite alone or in combination with the hydrotalcite in any of the preparation methods described herein.

In an embodiment, the hydrotalcite can be treated with an alkaline-earth or alkaline salt prior to being decomposed. In this embodiment, the hydrotalcite can be combined and suspended in a slurry of metal salt solution such as Mg-acetate or Ca-acetate and/or other alkaline or alkaline earth salts. The slurry is homogenized by mixing and heated to dryness followed by decomposition at high temperature, which causes hydrotalcite to thermally decompose (e.g., lose crystallinity and have the crystal structure collapse) as well as the metal salts to form corresponding oxides (e.g. MgO, CaO). Those oxides are strongly basic and they may be introduced to augment the aldol condensation catalytic ability of the catalyst. It is important to note that those salts are not introduced during the hydrotalcite synthesis and the metal ions are not exchanged into the hydrotalcite structure. As such they are not part of the structure and their amount could be varied independently of the components present in the hydrotalcite structure.

The resulting catalyst prepared as described herein has an improved performance both in terms of conversion and/or selectivity to higher alcohols. The difference in performance suggests that the catalytic materials have different microstructures that enable the significantly higher performance. It is likely that the coarser dispersion of the hydrogenation metal component or the fact that the dehydrogenation component is accessible by the reactant (the hydrogenation component is not buried in the decomposed hydrotalcite particles) allows for the catalyst component to achieve better performance. In an embodiment, the catalyst can comprise meixnerite ($Mg_6Al_2(OH)_{18} \cdot 4H_2O$), and the catalyst can be used alone or in combination with additional materials such as a magnesium aluminum spinel (e.g., $MgAl_2O_4$).

The resulting catalyst can include a powder that can be further processed for use in an alcohol conversion process. In an embodiment, a catalyst binder can be added to the catalyst to impart additional mechanical strength. For example, the resulting catalyst can be stirred into a colloidal suspension of silica or alumina in water. The resulting slurry can be extruded into pellets, granules, or other shapes, followed by heating at about 80-130° C. to dryness, and then calcined at temperatures between 300-1000° C.

The catalyst material composed of thermally decomposed hydrotalcite (and/or decomposed hydrocalumite) containing optional alkaline earth metal and dehydrogenation component (e.g., palladium, etc.) can be extruded into commercially applicable size and shape granules without the addition of support.

The catalyst can be prepared in different ways such as extrusion of the thermally decomposed hydrotalcite and/or decomposed hydrocalumite (with or without the optional alkali earth component) followed by loading the dehydrogenation component (e.g. Pd, etc.). Alternatively, the catalyst can be fully prepared as powder, including the deposition of the dehydrogenation component prior to extrusion. Despite the nearly identical composition by these two methods of preparation, the performance can be different due to different spatial distribution of the basic aldol condensation component and the dehydrogenation component (e.g., depositing the Pd after extrusion results in Pd aggregating on the pellet surface).

The resulting catalyst can be characterized in several ways. The catalyst can have a surface area of greater than about 20 $m^2/g$, greater than about 30 $m^2/g$, greater than about 40 $m^2/g$, or greater than about 50 $m^2/g$. In some embodiments, the surface area may be less than about 100 $m^2/g$, or less than about 90 $m^2/g$, or less than about 80 $m^2/g$. The surface area may be at least about 2, at least about 4, at least about 6, at least about 8, or at least about 10 times greater than the surface area of the starting synthetic or natural hydrotalcite, hydrocalumite, or both as applicable. The catalyst can have a pore volume of greater than about 0.05 $cm^3/g$, greater than about 0.1 $cm^3/g$, greater than about 0.2 $cm^3/g$, or greater than about 0.3 $cm^3/g$. In some embodiments, the pore volume may be less than about 0.4 $cm^3/g$, or less than about 0.35 $cm^3/g$. The pore volume may be at least about 2, at least about 4, at least about 6, at least about 8, or at least about 10 times greater than the pore volume of the starting synthetic or natural hydrotalcite. The surface area and the pore volumes may have any range between any lower values and any upper values. In some embodiments, the decomposition of the synthetic or natural hydrotalcite can form an amorphous mixture of aluminum and magnesium oxides, which at higher temperature can form meixnerite ($Mg_6Al_2(OH)_{18} \cdot 4H_2O$). The catalyst may also comprise a magnesium aluminum spinel (e.g., $MgAl_2O_4$)

While described as a single catalyst, the catalytic function can be obtained, in some embodiments, with a mixture of catalyst components. For example, a physical mixture of single purpose catalysts can be prepared to effectively create a dual-function catalyst system. In this embodiment, a catalyst (or catalysts) for alcohol dehydrogenation/aldehyde hydrogenation would be physically mixed with a catalyst (or catalysts) for aldol condensation. The use of a physical mixture may allow for use of less expensive base metals (Cu, Ni) as the preferred composition of the dehydrogenation/hydrogenation component of the catalyst instead of expensive noble-group metals.

Examples of the single purpose alcohol dehydrogenation/aldehyde hydrogenation catalyst include Cu, Ni, Pd, Ru, Pt, $Cr_2O_3$, $CuCr_2O_5$, Rh, Co, Fe, Ir, Os or any other commonly used heterogeneous hydrogenation catalyst supported on silica, silica-alumina, alumina, or activated carbon. These catalysts can be prepared via wetness impregnation of the support with an appropriate amount of the metal precursor salt in either an aqueous or other appropriate organic solution. The impregnated support would then be dried and calcined in air at temperatures between about 300° C. and about 550° C.

The aldol condensation catalyst component for the physical mixture can include the hydrotalcite materials (and/or the hydrocalumite materials) described above but without the addition of Pd or Cu salts. For example, aldol condensation catalyst component can comprise any of the decomposed hydrotalcite materials described herein. The hydrotalcite may be treated with an alkaline or alkaline earth oxide and thermally decomposed as described above.

In some embodiments, the catalyst can comprise one or more materials in place of the decomposed hydrotalcite. For example, the catalyst can comprise a magnesium aluminum spinel (e.g., $MgAl_2O_4$). The magnesium aluminum spinel can be treated with any of the additional components described above (e.g., having alkaline metal oxide such as MgO/CaO or Pd, Cu, etc. on $MgAl_2O_4$). In addition, the pelletization of the spinel materials can be done as described above for hydrotalcite. Extrusion can be done both prior to the deposition of the dehydrogenation component or after. The resulting catalyst can then be used in the production of n-butanol.

The catalysts described herein can be used with a number of processes to convert an alcohol to one or more higher alcohols. In general, the conversion process comprises contacting a reactant comprising an alcohol with the catalyst described herein at a reaction temperature and pressure sufficient to produce a reaction product. The reactor can include any suitable type of reactor such as a batch reactor, plug flow reactor, continuous stirred tank reactor, contact column, reactive distillation tower, or the like. The reaction can occur in the gas and/or liquid phase within the reactor. In some embodiments, the reactor containing the catalyst described herein can be used to convert ethanol to butanol or another higher alcohol (e.g., $C_5$-$C_{13}$ alcohols, or higher alcohols).

In some embodiments, the catalyst(s) described herein can be used with a reactive distillation system. In chemical processing, chemical reaction and the purification of the desired products by distillation may be carried out sequentially. The performance of this chemical process structure may be improved by the integration of reaction and distillation in a single multifunctional process system or unit. This integration concept is called "reactive distillation." The reaction may occur within the same vessel, or a second vessel in fluid communication with a separation vessel may be considered a reactive distillation. For example, a side reactor carrying out a reaction that is in fluid communication with a distillation column that removes at least a portion of the products would be considered a reactive distillation process. As advantages of this integration, chemical equilibrium limitations may be overcome, higher selectivities may be achieved, the heat of reaction may be used in situ for distillation, auxiliary solvents may be avoided, azeotropic and/or closely boiling mixtures may be more easily separated, or any combination thereof. Increased process efficiency and reduction in overall capital costs may result from the use of this approach.

A reactive distillation system comprises at least one separator (e.g., a distillation tower) in which a reaction is occurring and/or coupled to a vessel in which a reaction is occurring. In general, suitable separators may include any process equipment suitable for separating at least one inlet stream into a plurality of effluent streams having different compositions, states, temperatures, and/or pressures. For example, the separator may be a column having trays, packing, or some other type of complex internal structure. Examples of such columns include scrubbers, strippers, absorbers, adsorbers, packed columns, and distillation columns having valve, sieve, or other types of trays. Such columns may employ weirs, downspouts, internal baffles, temperature control elements, pressure control elements, or any combination thereof. Such columns may also employ some combination of reflux condensers and/or reboilers, including intermediate stage condensers and reboilers. In an embodiment, the reactive distillation system described herein may comprise a distillation tower.

As indicated above, the catalyst(s) described herein can be used in systems and methods for the production of higher alcohols from ethanol. The present disclosure further provides improved processes for the production of one or more high purity higher alcohols from a lighter alcohol feed or from a feedstock comprising a major proportion of a lighter alcohol feed and a minor proportion of impurities such as iso-propanol, iso-butanol, water, or any combination thereof. While not commonly present in alcohol feed streams, impurities that can poison the particular catalyst used should be limited, avoided and/or removed. For example, sulfur or nitrogen heterocyclic compounds can frequently act as catalyst poisons and, if present, should be removed before introducing the alcohol feed stream to the reactive distillation column.

With respect to the alcohol forming the reactant in the formation process, the present description is generally described in terms of ethanol. However, a number of alcohols can form the reactant. In some embodiments, the process is believed to occur with a feed comprising any alcohol comprising an alpha hydrogen in regard to the hydroxyl group (e.g., an alpha hydrogen alcohol) including, but not limited to, a primary or secondary alcohol. In an embodiment, the feed may comprise one or more alcohols other than methanol and may include any $C_2$-$C_5$ alpha hydrogen alcohols. In addition to ethanol, additional alcohols can be used in the reaction feed including, but not limited to, propanol, isopropanol, butanol, isobutanol, pentanol, etc.

The present systems and methods provide a reactive distillation system in which an alcohol feed comprising an alcohol having an alpha hydrogen is fed to a reactive distillation system. In an embodiment, ethanol may be the sole or primary component of the feed. Reference to a "single feed" to a reactive distillation column means that the column has only one chemical feed stream supplying intended reactant(s) to the column. Nonetheless, such a single feed distillation column may have multiple entry points for the reactant, or recycling feed streams where a part of the reactant liquid or a partial distillate is drawn from the column and fed back into the column at a different point, e.g., to achieve improved separation and/or more complete reaction.

The single feed may comprise a single reactant such as an alpha hydrogen alcohol (e.g., ethanol). A "single alcohol feed" refers to a feed stream of a single alpha hydrogen alcohol, and a "single ethanol feed" refers to a single feed stream in which ethanol is the sole or at least the primary constituent. In contrast, the term "dual feed" in the context of a distillation column refers to two separate chemical feed streams. For example, in some of the present embodiments, dual feeds can include an ethanol feed stream and a separate hydrogen feed stream. The term "reactive distillation system" is used conventionally to refer to a distillation column in which separation is performed while a reaction is occurring. The reaction may occur within the same distillation column and/or within a second vessel in fluid communication with a distillation column may still be considered a reactive distillation column. For example, a side reactor carrying out a reaction that is in fluid communication with a distillation column that removes at least a portion of the products would be considered a reactive distillation process occurring in a reactive distillation system.

In general, higher alcohols are produced by the addition of one or more lighter alcohols and/or side products. In embodiments where the production of n-butanol is desired, the primary and desired reaction is the conversion of two ethanol molecules to one butanol molecule with release of one water molecule. To this end, the present application provides systems and methods for the production of higher alcohols from an alpha hydrogen alcohol such as ethanol, which includes reacting one or more alpha hydrogen alcohols over the catalyst(s) described herein in a reactive distillation system, thereby producing higher alcohols and water. To this end, the present application provides catalysts along with systems and methods for the production of higher alcohols from an alpha hydrogen alcohol, which includes reacting one or more alpha hydrogen alcohols over the catalyst(s) in a reactive distillation system, thereby producing one or more higher alcohols, and water. In some embodiments byproducts may also be produced as described in more detail herein.

In an embodiment, a single reactive distillation column is used. Water can be removed (e.g., continuously) from the top of the reactive distillation column as an overhead stream. In some embodiments, the overhead stream may comprise some amount of the alpha hydrogen alcohol(s) present in the feed such as ethanol. Higher alcohols can be removed (e.g., continuously) from the bottom of the column as a bottoms stream. Optionally, contaminating byproducts present following reaction of the alpha hydrogen alcohol(s) over the conversion catalyst can be reacted over a suitable hydrogenating catalyst in the lower part of the column or in a separate hydrogenation reactor. The hydrogenation can convert difficult to separate byproducts into species which are easier to separate from the higher alcohol(s). Consequently, the process can also include purifying the higher alcohols, including separating one or more higher alcohols, by distilling out resulting hydrogenated byproducts.

In its simplest form, a reactive distillation system may comprise a reactor vessel operating with a liquid and/or gas phase reaction in which water and any unreacted alpha hydrogen alcohols are removed as the overhead product and a reaction product is removed as the bottoms product. The reactor vessel can comprise a continuous stirred-tank reactor (CSTR). Alternatively, such a system may comprise a batch reactor in which water and any unreacted alpha hydrogen alcohols are removed during the reaction and the liquid product is removed after completion of the reaction to a desired degree of conversion.

In an embodiment, a reactive distillation column with a single feed of an alpha hydrogen alcohol(s) as shown in FIG. 1 can produce byproducts including hydrogen as an overhead stream 10, water as a distillate stream 9, and higher alcohols (e.g., $C_4$-$C_{13}$ alcohols such as n-butanol, or higher alcohols) as a bottoms product stream 15. In general, the alpha hydrogen alcohol feed can comprise any primary alcohol other than methanol and may include any $C_2$-$C_5$ alpha hydrogen alcohols. In an embodiment, the alpha hydrogen alcohol feed stream 4 can comprise ethanol, butanol, and/or propanol. In some embodiments, the alpha hydrogen alcohol feed stream may comprise ethanol as the only alpha hydrogen alcohol. The alpha hydrogen alcohol is fed as a feed stream 4 to the reactive distillation column 1. The column reflux and reboil ratios are maintained such that high recovery of higher alcohols is obtained in the bottoms stream 15. The higher alcohols and by-products are produced due to the reaction over the catalyst 7. The catalyst(s) 7 may include any of the catalysts described or referenced above. The reactants and products may flow through the reactor/column reacting and flashing along the length of the reactor/column. In some embodiments, the alpha hydrogen alcohol may react in the liquid phase over the catalyst 7 to produce the higher alcohols. The removal of the higher alcohols and the by-products during the distillation may increase the extent of reaction. The column conditions can be controlled to alter or tune the product distribution. For example, the temperature in the reaction zone (e.g., the zone in which the reacts are in contact with the catalyst) and/or the contact time (e.g., as controlled by reflux/reboil ratios, column holdup, etc.) can be controlled to provide a desired higher alcohol product distribution.

Unconverted alpha hydrogen alcohols (e.g., ethanol) in the feed that may be carried with the distillate stream is condensed (e.g., in condenser 6 and separated in flash tank 8) and refluxed back into the column 1. Continuous removal of the higher alcohols and the by-products such as water from the reactive distillation column moves the reaction forward. The higher alcohols and other heavy boiling components leave in the bottoms stream 15 of the reactive distillation column 1. The column 1 can be operated between a pressure of about 1 atm and about 100 atm. The temperature profile in the column 1 is dictated by the mixture's boiling point along the height of the column. High conversion of the alpha hydrogen alcohol feed to products can be achieved by the counter-current flow of reactants and products in addition to overcoming the reaction equilibrium by removal of products. The bottoms product stream 15 can be separated to provide a stream comprising predominantly lighter alcohols (e.g., $C_2$-$C_4$ alcohols) and a stream comprising predominantly higher alcohols. The higher alcohols stream may be purified to comprise greater than about 90%, greater than about 95%, greater than about 98%, greater than about 99%, or greater than about 99.5% pure higher alcohols. The number of stages (or HETP in case of a packed column) for the column 1 can range from about 2 to about 100. The lighter alcohols stream can be removed as a separate product stream and/or recycled to the feed stream 4 for further reaction within the column 1.

While illustrated as having the catalyst 7 disposed within the central portion of the column 1, the catalyst 7 may be located only above or below the alpha hydrogen alcohol feed location. In an embodiment, the catalyst 7 may be disposed only above the feed location, and the lower portion of the column may comprise trays, packing, or the like to provide a stripping section. In some embodiments, the catalyst 7 may be disposed only below the feed location, and the upper portion of the column may comprise trays, packing, or the like to provide a rectifying section.

Figure 2:
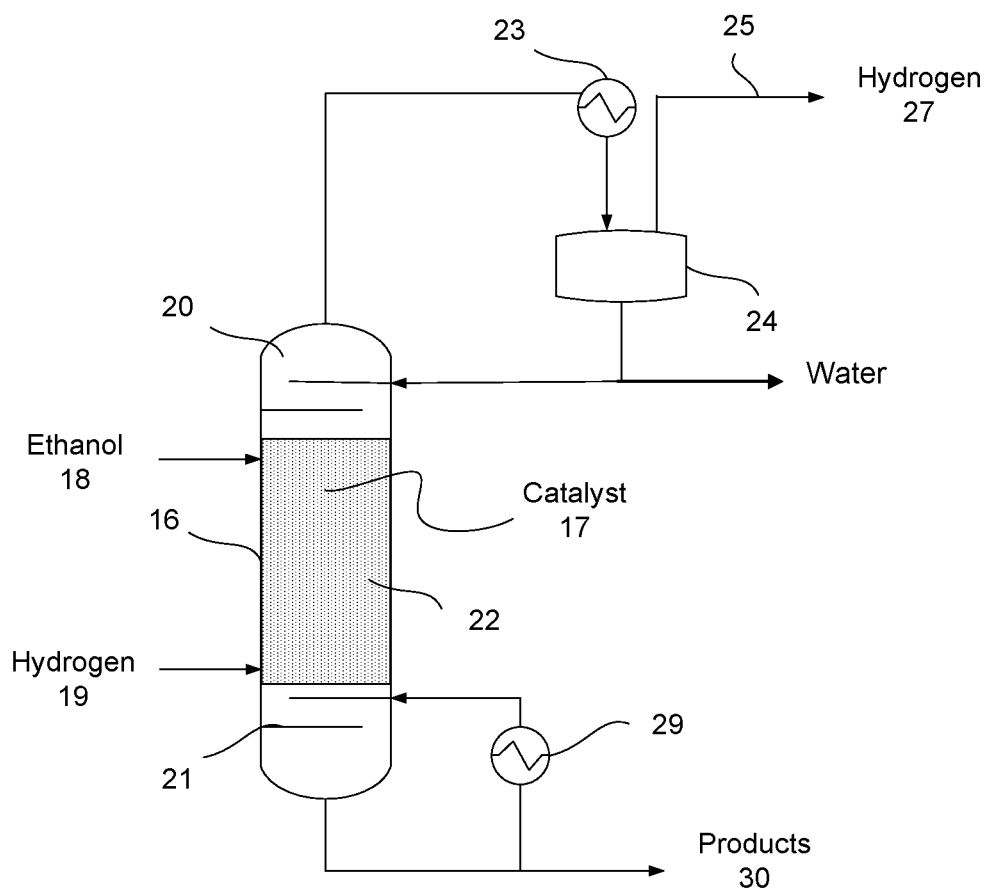
FIG. 2 shows another simplified schematic of a reactive distillation system according to still another embodiment.

FIG. 2 shows a process schematic for a reactive distillation column 16 with dual feed (alpha hydrogen alcohol feed 18 and hydrogen feed 19). The alpha hydrogen alcohol feed 18 is fed to the upper part of the column 16 (upper feed 18). Hydrogen is fed to the lower part of the column (lower feed 19). Due to boiling point difference, hydrogen moves towards the top of the column 16 and the alpha hydrogen alcohol moves towards the bottom of the column 16, thereby allowing the alpha hydrogen alcohol to react over the catalyst 17 in the column 16 in the presence of hydrogen. The excess hydrogen may cause the intermediate aldehydes to be hydrogenated more readily, potentially allowing for more selectivity to the shorter alcohols, such as 1-butanol. Conversion of the alpha hydrogen alcohols may or may not be affected by the addition of hydrogen to the reactor feed. In a reactive distillation the addition of hydrogen could occur at the very bottom of the column or anywhere along the length of the column where the reactive catalyst and/or packing is located. The reactive distillation column 16 may be operated between a pressure of about 1 atm and about 100 atm. The reactive distillation column 16 may otherwise be the same or similar to the reactive distillation column of FIG. 1.

Figure 3:
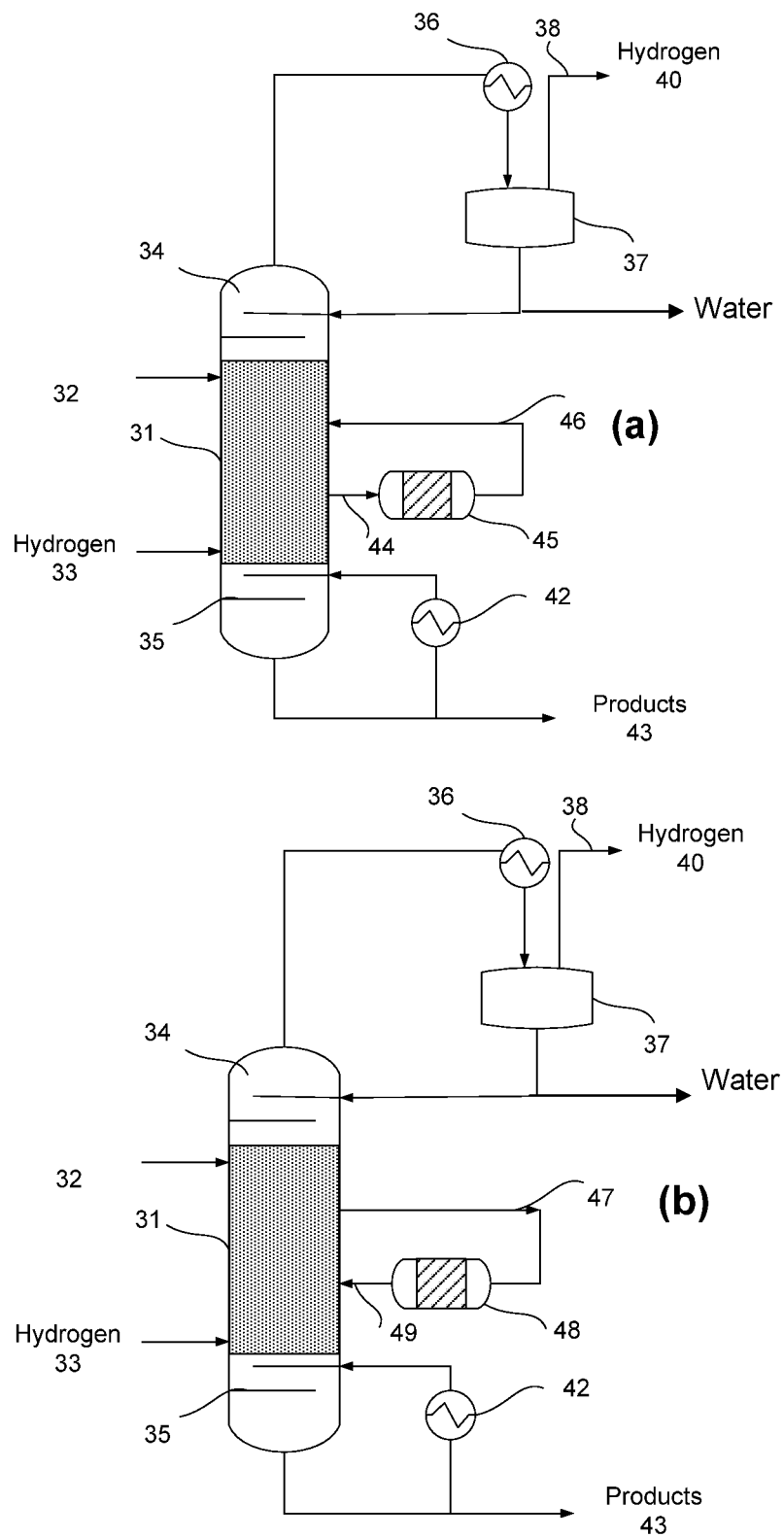
FIGS. 3(a) and 3(b) shows a simplified schematic of a reactive distillation system according to yet another embodiment.

FIG. 3 (a) shows a process schematic for a reactive distillation column 31 with dual feed (alpha hydrogen alcohol feed 32 and hydrogen feed 33). While dual feeds are illustrated, a single feed may be used, such as a single feed of an alpha hydrogen alcohol. One or more side reactors, such as side reactor 45, can be utilized to increase the amount of residence time available for the reaction. As illustrated, the side reactor 45 can comprise a catalyst as described herein. Stream 44 can be in the gas phase and react over the catalyst in side reactor 45. FIG. 3 (b) shows a process schematic for a reactive distillation column 31 with dual feed (alpha hydrogen alcohol feed 32 and hydrogen feed 33). A side reactor 48 can be utilized to increase the amount of residence time available for the reaction. Stream 47 is in liquid phase and can react over the catalyst in side reactor 48 (e.g., the liquid reacts in the liquid phase over the catalyst). In some embodiments, catalyst can be present only in the side reactor or in the side reactor and the column. In some embodiments, the catalyst may be present in only the side reactor, and the column may not comprise a catalyst.

In some embodiments, one or more of the feeds (e.g., alpha hydrogen alcohol feed 32 and hydrogen feed 33) could be introduced directly into the side reactors prior to entering the distillation column. For example, the alpha hydrogen alcohol feed 32 could enter the side reactor or be combined with the stream from the column prior to entering the side reactor. This may be useful in embodiments in which the distillation column does not comprise a catalyst.

Figure 4:
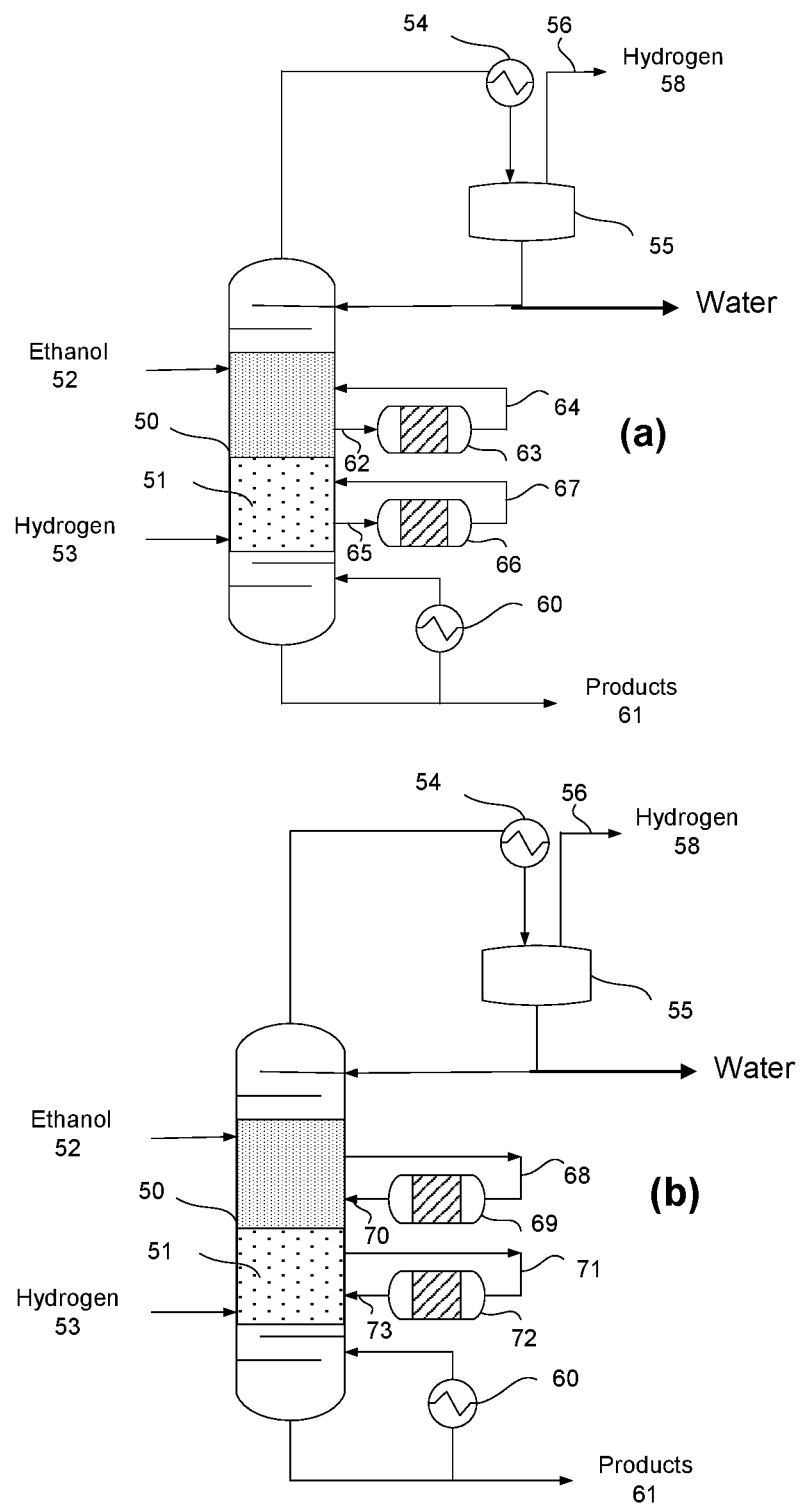
FIGS. 4(a) and 4(b) shows a simplified schematic of a reactive distillation system according to still another embodiment.

FIG. 4 (*a*) shows a process schematic for a reactive distillation column with dual feed (alpha hydrogen alcohol and hydrogen). While dual feeds are shown in FIG. 4(*a*), only a single feed of an alpha hydrogen alcohol may be present. Multiple side reactors can be utilized to increase the amount of residence time available for the reaction. Feed streams represented by 62 and 65 are in the gas phase and react over the catalyst (e.g., any of the catalysts described herein) in side reactors represented by 63 and 66. FIG. 4(*b*) shows a process schematic for a reactive distillation column with dual feed (alpha hydrogen alcohol and hydrogen). Multiple side reactors can be utilized to increase the amount of residence time available for the reaction. Streams represented by 68 and 71 can be in the liquid phase and react over the catalyst in side reactors represented by 69 and 72. A plurality of side reactors can be used in the configurations shown in FIG. 4. In some embodiment, catalyst can be present only in the side reactor, and the column may not comprise a catalyst.

As illustrated in FIG. 4(*a*) and FIG. 4(*b*), the column 50 may comprise two catalysts. For example, two different catalysts may be present in the column. The catalysts may comprise the same or different components. Similarly, when a plurality of side reactors are present, the catalysts in each side reactor may be the same or different. The different reaction conditions in the different portions of the column and the different side reactors may be taken into account when determining the catalyst or catalysts to include in each area. In some embodiments, the catalysts used in the column and/or the side reactors may be the same.

As a general proposition, the number of side reactors and the type of catalyst with which the column and each side reactor are individually charged can be selected to accommodate a desired variety of feedstocks, a desired range of product compositions, or a combination thereof during operation of the reactive distillation column. During continuous operation, the flow rates between the side reactors and the column can be adjusted (e.g., selectively tuned) to respond to changes in feedstock, to achieve a desired product composition, or a combination thereof. The ability to adjust the flow rates between the side reactors and the column advantageously allows feedstocks to be changed when market fluctuations in price and availability favor the use of a feedstock having a different composition (e.g. lower quality, higher water content, different mix of alpha hydrogen alcohols, etc.). The ability to adjust the flow rates between the side reactors and the column advantageously allows feed quality to be maintained despite fluctuations in feedstock composition during continuous operation. The ability to adjust and/or control the flow rates between the side reactors and the column may also allow for the reduction or elimination of undesirable byproducts to advantageously increase the purity of the desired products. In some embodiments, the catalyst(s) may only be present in the side reactors and not in the distillation column.

As noted above, one or more of the feeds (e.g., alpha hydrogen alcohol feed 52 and hydrogen feed 53) could be introduced directly into the side reactors prior to entering the distillation column. For example, the alpha hydrogen alcohol feed 52 could enter the side reactor or be combined with the stream from the column prior to entering the side reactor. This may be useful in embodiments in which the distillation column does not comprise a catalyst.

Figure 5:
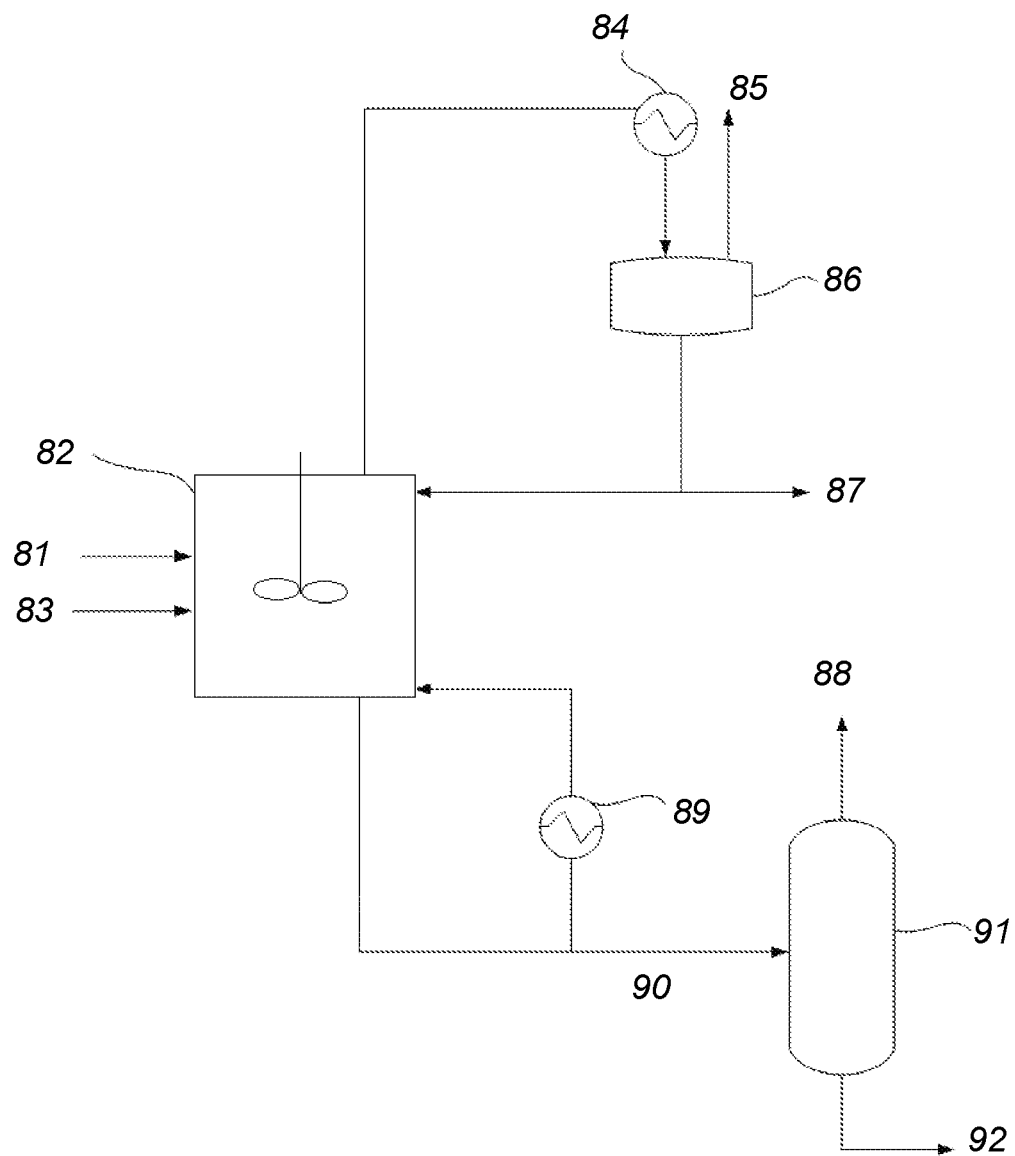
FIG. 5 shows a simplified schematic of a reactive distillation system according to an embodiment.

Another embodiment of a system for producing higher alcohols is shown in FIG. 5. In this embodiment, the reactive distillation system may comprise a continuous stirred-tank reactor (CSTR) 82, which can comprise a catalyst as described herein, that is coupled to a phase separator 91 and configured for the dehydration of an alpha hydrogen alcohol with the formation of one or more higher alcohols. In an embodiment, production of higher alcohols may be accomplished by passing the feed stream 81, which comprises a feed of an alpha hydrogen alcohol or an alpha hydrogen alcohol and optionally hydrogen in stream 83, into the CSTR 82 wherein the feed mixes and contacts the catalyst under conditions where higher alcohols and water are formed. As the conversions proceed, the resulting mixture may pass to a phase separator 91 from which the water leaves as distillate 88 and higher alcohols including any butanol or heavier alcohols can leave as a bottom product 92. Phase separator 91 may be any phase separator, which is a vessel that separates an inlet stream into a substantially vapor stream and a substantially liquid stream, such as a knock-out drum, flash drum, reboiler, condenser, or other heat exchanger. Such vessels also may have some internal baffles, temperature control elements, pressure control elements, or any combination thereof, but generally lack any trays or other type of complex internal structure commonly found in columns.

Figure 6:
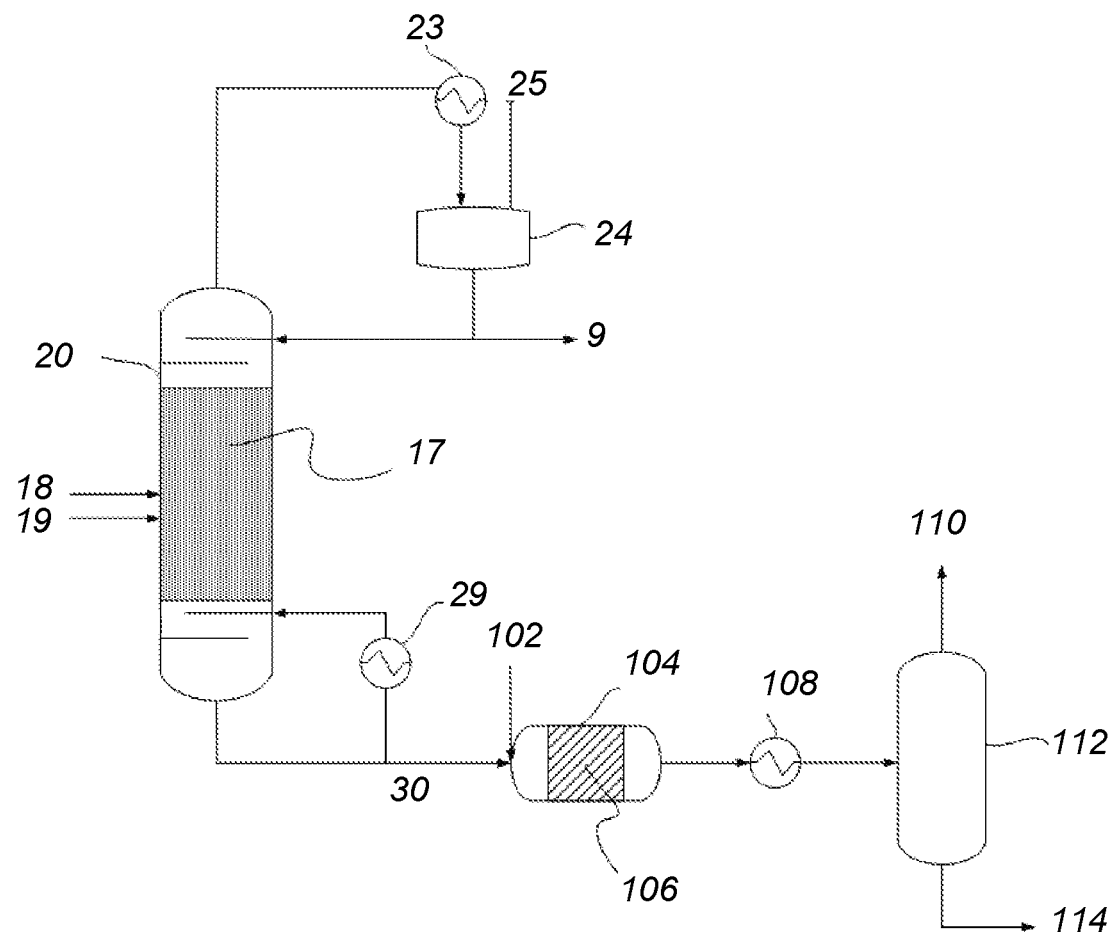
FIG. 6 shows a simplified schematic of a reactive distillation system according to another embodiment.

FIG. 6 shows a process schematic where the bottoms product 30 from the reactive distillation column 20 illustrated in FIG. 2 is sent to a hydrogenation reactor 104 comprising a hydrogenating catalyst 106 with a hydrogen co-feed in stream 102. Suitable hydrogenating catalyst(s) may comprise various components and are described in more detail herein. At least a portion of the byproducts can be hydrogenated in the hydrogenation reactor 104, pass through heat exchanger 108, and can then be separated using a separator 112. The separator 112 may comprise any of the types of separators described herein with respect to the reactive distillation system. Alternatively or in addition to the separators already described, the separator 112 may be a phase separator, which is a vessel that separates an inlet stream into a substantially vapor stream and a substantially liquid stream, such as a knock-out drum, flash drum, reboiler, condenser, or other heat exchanger. Such vessels also may have some internal baffles, temperature control elements, pressure control elements, or any combination thereof, but generally lack any trays or other type of complex internal structure commonly found in columns. The separator 112 also may be any other type of separator, such as a membrane separator. In a specific embodiment, the separator is a knockout drum. Finally, the separator may be any combination of the aforementioned separators arranged in series, in parallel, or combinations thereof. In an embodiment, separator 112 comprises a distillation column. The outlet of the hydrogenation reactor 104 may be passed through a heat exchanger 108 (e.g., a condenser) and cooled before entering the separator 112. The heat exchanger 108 may be any equipment suitable for heating or cooling one stream using another stream. Generally, the heat exchanger 108 is a relatively simple device that allows heat to be exchanged between two fluids without the fluids directly contacting each other. Examples of suitable heat exchangers 108 include, but are not limited to, shell and tube heat exchangers, double pipe heat exchangers, plate fin heat exchangers, bayonet heat exchangers, reboilers, condensers, evaporators, and air coolers. In the case of air coolers, one of the fluids comprises atmospheric air, which may be forced over tubes or coils using one or more fans.

The bottoms product stream 114 from the separator 112 may comprise one or more higher alcohols (e.g., butanols, pentanols, etc.) and may have a purity of greater than about 90%, greater than about 95%, greater than about 96%, greater than about 97%, greater than about 98%, greater than about 99%, or greater than about 99.5% by weight. Unconverted water and the hydrogenated byproducts may be removed as an overhead product 110, and may be used, for example, as fuel or a feed to one or more processes. In an embodiment, the separator 112 may be operated between a pressure of 1 atm and 80 atm.

In an embodiment, the bottoms product stream 114 may pass to another separator. The separator may then separate the bottoms product stream into a higher alcohols stream and a byproduct stream comprising one or more heavier hydrogenation products produced in the hydrogenation reactor 104. The components within a mixed higher alcohols stream can be further separated to produce one or more product streams comprising predominately individual higher alcohols. This separation scheme may allow for one or more resulting higher alcohol streams to have individual component purities of greater than about 90%, greater than about 95%, greater than about 96%, greater than about 97%, greater than about 98%, greater than about 99%, or greater than about 99.5% of the respective higher alcohol by weight. In an embodiment, the product stream may have a purity of greater than about 90%, greater than about 95%, greater than about 96%, greater than about 97%, greater than about 98%, greater than about 99%, or greater than about 99.5% n-butanol by weight.

Figure 7:
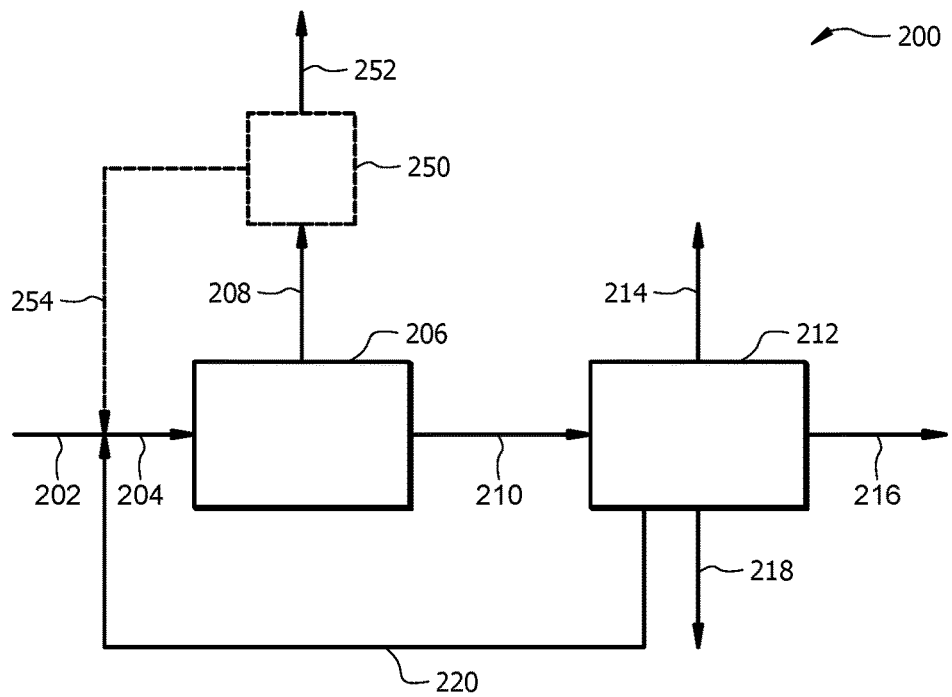
FIG. 7 illustrates a schematic flow diagram of a reactive distillation system with a recycle according to an embodiment.

As schematically illustrated in FIG. 7(a), a higher alcohols production process may comprise a products separation section 212 for use in separating the product stream and allowing at least a portion of any unreacted ethanol to be recycled to the inlet of the process. The products separation section may be configured to provide at least one product stream comprising a single reaction product such as a higher alcohol (e.g., propanol, butanol, hexanol, etc.), or another reaction product having a purity of greater than about 90%, greater than about 95%, greater than about 96%, greater than about 97%, greater than about 98%, greater than about 99%, or greater than about 99.5% by weight. In an embodiment, a separation train may be used to produce a plurality of streams that each predominately comprise a single reaction product such as a higher alcohol (e.g., propanol, butanol, hexanol, etc.), or another reaction product having a purity of greater than about 90%, greater than about 95%, greater than about 96%, greater than about 97%, greater than about 98%, greater than about 99%/o, or greater than about 99.5% by weight. At least one additional stream may be produced comprising the remaining components of the product stream from the reactive distillation column. In an embodiment, a plurality of streams are produced in the separation section comprising a stream predominantly comprising butanol, a stream predominantly comprising propanol, a stream predominantly comprising hexanol, a stream comprising water, a stream comprising ethanol, a heavies stream comprising one or more reaction products with boiling points above the boiling point of hexanol, or any combination thereof. In an embodiment, a stream comprising ethanol, if present, may be recycled to the reactive distillation column.

As schematically illustrated in FIG. 7(a), a system 200 for producing one or more higher alcohols may comprise a feed stream 202 comprising an alpha hydrogen alcohol that may be optionally combined with a recycle stream 220 comprising an alpha hydrogen alcohol to form the inlet stream 204 to the reactive distillation system 206. The system 200 may be useful for embodiments in which there is an incomplete conversion of an alpha hydrogen alcohol in the reactive distillation system 206. While illustrated as being combined prior to introduction to the reactive distillation system 206, the feed stream 202 and the recycle stream 220 may be fed individually to the reactive distillation system 206. In an embodiment, the reactive distillation system 206 may comprise any of the reactive distillation systems described with respect to FIGS. 1-6 herein. The reactive distillation system 206 may produce an overhead product stream 208 and a bottoms product stream 210. The overhead product stream 208 may comprise water, hydrogen, unreacted alpha hydrogen alcohol(s), or a combination thereof and may generally correspond to any of these streams as illustrated in FIGS. 1-6. Similarly, the bottoms product stream 210 may comprise higher alcohols (e.g., butanol, 1-hexanol, 1-octanol, 2-ethyl-1-butanol, 2-ethyl-1-hexanol, butanediol, etc.), ethyl butyrate, 2-pentanone, propanol, additional reaction products, possibly water, and/or any combination thereof. In an embodiment, the bottoms product stream 210 may correspond to any of these streams as illustrated in FIGS. 1-6.

An optional overhead separation section 250 may receive the overhead product stream 208 from the reactive distillation system 206. The overhead separation section 250 may be configured to separate water from any alpha hydrogen alcohol(s) (e.g., ethanol) in the overhead product stream 208, which may be present at a water-alcohol azeotrope such as a water-ethanol azeotrope, to allow the feed alpha hydrogen alcohol to be recycled to the system while removing the water to drive the reaction within the reactive distillation system 206. The overhead separation section 250 may comprise any number or type of separation units, which may employ pressure- and/or temperature-swing distillation, pressure- and/or temperature-swing adsorption, membrane-based separation, molecular sieve separation, any other suitable separation technology, or any combination thereof, all of which may be used to remove a desired amount of water from the overhead product stream 208. The overhead separation section 250 may produce a recycle stream 254 comprising one or more alpha hydrogen alcohols and an outlet stream 252 comprising water. The recycle stream 254 may comprise the alpha hydrogen alcohol(s) for use as a feed for the reactive distillation system 206. In some embodiments, the alpha hydrogen alcohol stream 254 may not be recycled to the reactive distillation system, but rather may exit the system 200 as a separate product stream. While illustrated as being combined prior to introduction to the reactive distillation system 206, the feed stream 202 and the recycle stream 254 (as well as recycle stream 220) may be fed individually to the reactive distillation system 206.

A products separation section 212 may receive the bottoms product stream 210 from the reactive distillation system 206, and, in some embodiments, the overhead product stream 208. The products separation section 212 may comprise any number or type of separation units, which may employ pressure- and/or temperature-swing distillation, pressure- and/or temperature-swing adsorption, membrane-based separation, cryogenic distillation, any other suitable separation technology, or any combination thereof, all of which may be used to generate a desired product distribution. The products separation section 212 may generally produce one or more product streams such as product stream 216. The higher alcohol product stream 216 may comprise a higher alcohol having a purity of greater than about 90%, greater than about 95%, greater than about 96%, greater than about 97%, greater than about 98%, greater than about 99%, or greater than about 99.5% by weight. In addition to the higher alcohol product stream 216, one or more additional streams may be produced by the products separation section 212. In an embodiment, a lights product stream 214 may be produced. The lights product stream 214 may comprise water, any alpha hydrogen alcohol from the feed, hydrogen, other light components, or any combination thereof. In an embodiment, a heavies product stream 218 may comprise one or more reaction products (e.g., one or more aldehydes, ketones, heavy alcohols, any combination thereof, etc.). In an embodiment, a recycle stream 220 may be produced. The recycle stream may comprise one or more alpha hydrogen alcohols for use as a feed for the reactive distillation system 206. In some embodiments, the alpha hydrogen alcohol(s) stream may not be recycled to the reactive distillation system, but rather may exit the system 200 as a separate product stream. Each of the potential product streams 214, 216, 218, and/or 220 may exit the system as separate product stream and/or exit the system 200 for use as fuel and/or as a feed to additional downstream processes. While illustrated as separate streams 214, 216, 218, and/or 220, one or more of these streams may exit the system 200 as a combined product stream.

The higher alcohols production process may produce a variety of products. For example, the process may produce one or more higher alcohols such as butanol, propanol, 1-hexanol, 1-octanol, 2-ethyl-1-butanol, 2-ethyl-1-hexanol, butanediol, and heavier alcohols. The process may also produce various additional products such as ethyl acetate, butyl acetate, ethyl butyrate, 2-pentanone, propanol, and/or water. Various side products may also be produced that can result in a complex mixture of components that can be difficult to separate. This complex mixture may exhibit a number of binary azeotropes, ternary azeotropes, and possibly azeotropes containing four or more components. Some of the azeotropes can be homogeneous, while others can be heterogeneous. These azeotropes can give rise to distillation boundaries in the composition space that, along with the azeotropes, act as barriers for distillation and limit the ability to achieve high recovery and/or purity of the desired products using distillation alone. When water is present in a sufficient amount, the system may also comprise a multiple liquid phase region, with vapor-liquid-liquid and/or liquid-liquid equilibrium tie-lines that cross some of these boundaries. In some embodiments, a product separation system can exploit this characteristic of the system and comprise a separation sequence comprising distillation columns and decanters. This system may be capable of producing one or more high purity product streams such as one or more high purity higher alcohol stream, an ethyl acetate stream, and potentially one or more other valuable byproduct streams.

In some embodiments, conventional, separate reactors and distillation systems can be used to carry out the reaction steps sequentially. For example, one reactor would be used to selectivity convert ethanol to higher alpha hydrogen alcohols and a second reactor can be used to selectively convert the higher alpha hydrogen alcohols to higher alcohols. The resulting higher alcohols stream can be used for a variety of commercial processes including as precursors to various polymers, industrial solvents, and the like. In some embodiments, the higher alcohols can be further converted to ethers, esters or the like.

In an embodiment, the higher alcohol can comprise butanol, which can be further processed into various fuel components. For example, the higher alcohol product can be contacted, with or without a solvent, with one or more acid catalysts (e.g., sulfuric acid, heteropoly acids, natural clay minerals, cation exchanged resins, metal oxides, mixed metal oxides, metal salts, zeolites, perfluorinated ion-exchanged polymers, ion-exchanged resins, mixtures thereof, etc.) at a temperature between about 50° C. and about 450° C. and at a pressure between about 0.1 MPa and about 21 MPa to produce a reaction product comprising two or more ethers (e.g., dialkyl ethers, etc.). The resulting ethers can be used in various ways including as an additive for a fuel mixture. More details on the conversion of a higher alcohol product comprising butanol to ethers can be found in U.S. Pat. No. 8,398,728 to Ozer et al. and U.S. Patent Application Publication No. 2010/0197974 to Harmer et al., both of which are incorporated by reference herein in its entirety.

For the systems described herein comprising a hydrogenation catalyst or catalysts, the hydrogenating catalyst generally can include a Group VIII metal and/or a Group VI metal. Examples of such a catalyst can include, but is not limited to, Cu, Re, Ni, Fe, Co, Ru, Pd, Rh, Pt, Os, Ir, and alloys, oxides (e.g., $PtO_2$), or any combination thereof, either alone or with promoters such as W, Mo, Au, Ag, Cr, Zn, Mn, Sn, B, P, Bi, and alloys, oxides (e.g., $Cr_2O_3$, $Cu_2Cr_2O_5$), or any combination thereof. Other effective hydrogenating catalyst materials include either supported nickel or ruthenium modified with rhenium. In an embodiment, the hydrogenating catalyst also includes any one of the supports described below, depending on the desired functionality of the catalyst. The hydrogenating catalysts may be prepared by methods known to those of ordinary skill in the art.

In an embodiment, the hydrogenating catalyst includes a supported Group VIII metal catalyst and a metal sponge material (e.g., a sponge nickel catalyst such as Raney nickel). Raney nickel provides an example of an activated sponge nickel catalyst suitable for use in this invention. In an embodiment, the hydrogenation reaction in the invention is performed using a catalyst comprising a nickel-rhenium catalyst or a tungsten-modified nickel catalyst. One example of a suitable catalyst for the hydrogenation reaction of the invention is a carbon-supported nickel-rhenium catalyst.

In an embodiment, a suitable Raney nickel catalyst may be prepared by treating an alloy of approximately equal amounts by weight of nickel and aluminum with an aqueous alkali solution, e.g., containing about 25 wt % of sodium hydroxide. The aluminum is selectively dissolved by the aqueous alkali solution resulting in a sponge shaped material comprising mostly nickel with minor amounts of aluminum. The initial alloy includes promoter metals (e.g., molybdenum or chromium) in the amount such that 1 to 2 wt % remains in the formed sponge nickel catalyst. In another embodiment, the hydrogenating catalyst is prepared using a solution of ruthenium(III) nitrosylnitrate or ruthenium (III) chloride in water to impregnate a suitable support material. The solution is then dried to form a solid having a water content of less than 1% by weight. The solid is then reduced at atmospheric pressure in a hydrogen stream at 300° C. (uncalcined) or 400° C. (calcined) in a rotary ball furnace for 4 hours. After cooling and rendering the catalyst inert with nitrogen, 5% by volume of oxygen in nitrogen is passed over the catalyst for 2 hours.

In certain embodiments, the hydrogenating catalyst may include a catalyst support to support and stabilize the catalyst. The type of catalyst support used depends on the chosen catalyst and the reaction conditions. Suitable supports may include, but are not limited to, carbon, silica, silica-alumina, alumina, zirconia, titania, ceria, vanadia, boron nitride, heteropolyacids, hydroxyapatite, zinc oxide, chromia, zeolites, carbon nanotubes, carbon fullerenes, and any combination thereof. The hydrogenating catalyst can be employed in any of the conventional types or structures known to the art. In an embodiment, any of the catalyst shapes and/or types discussed herein with respect to the conversion catalyst may be used with the hydrogenating catalyst.

EXAMPLES

The disclosure having been generally described, the following examples are given as particular embodiments of the disclosure and to demonstrate the practice and advantages thereof. It is understood that the examples are given by way of illustration and are not intended to limit the specification or the claims in any manner.

Example 1

Catalyst Example 1

15 g of synthetic hydrotalcite were mixed with 4 g of solid Ca-hydroxide and ~50 ml water to form a thick slurry. Ethanol was added until all solids were wetted by the water. The slurry was mixed very well, dried at 105° C. followed by heating to 475° C. at a heating rate of 1° C./min and held at 475° C. for 2 hours followed by cooling to room temperature. A 7 g sample from the resulting powder was mixed into a wet paste with ~15 ml aqueous solution of 0.1025 g $Pd(NO_3)_2 \cdot 6H_2O$. The paste was dried at 105° C., and the dry powder was treated with 0.5 ml 4 M NaOH, 1 ml 35 wt. % stock aqueous methanol formaldehyde solution diluted to 7 ml with DI water. A color transformation took place indicating the reduction of the Pd salt to Pd metal. The resulting powder was pressed into pellets, broken down to uniform sizes and subjected to testing for ethanol to n-butanol and higher alcohols conversion.

Figure 8:
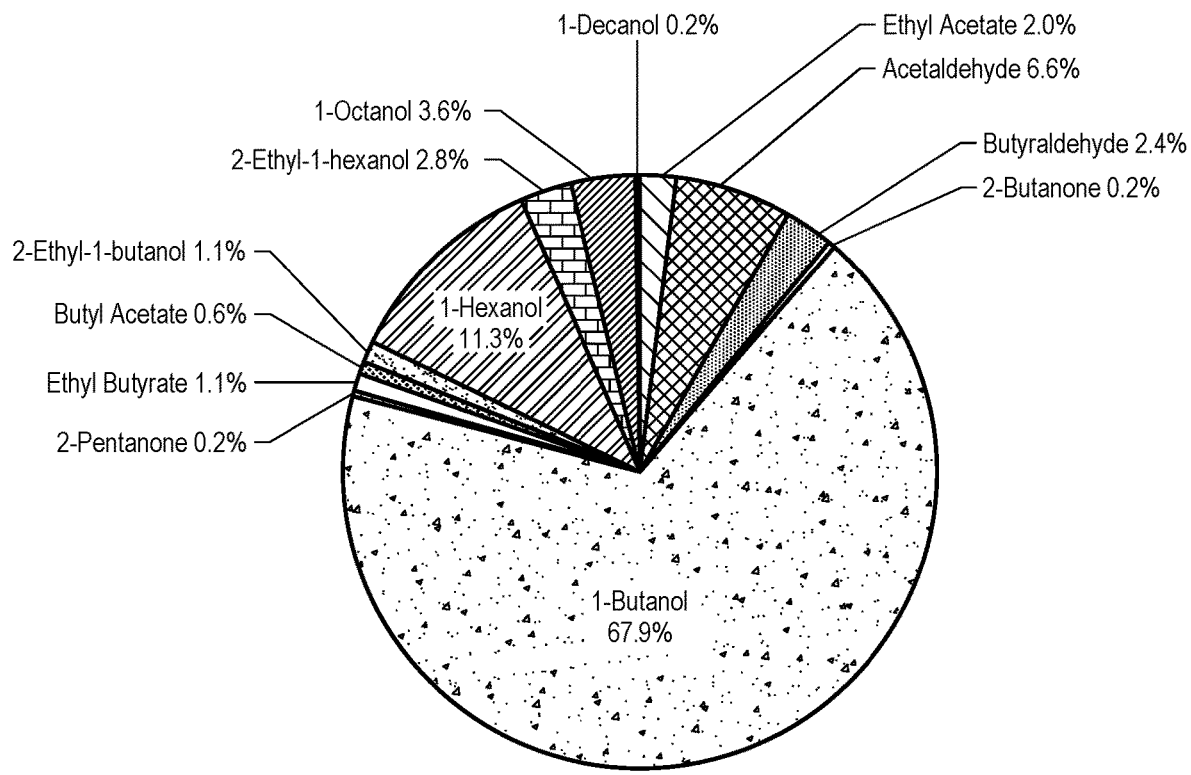
FIG. 8 illustrates a product distribution obtained by reacting ethanol over an embodiment of the catalyst.

The testing used 4.3 g of the catalyst at 260° C. and 300 psig pressure, with a flow rate of ethanol of 0.2 ml/min. The product distribution achieved is shown in FIG. 8, which illustrates an ethanol conversion of 13.9%.

Table 1 shows the ethanol conversion and selectivity to both 1-butanol and to all alcohols in the $C_4$-$C_{12}$ range at different temperatures and at testing conditions using 4.3 g of the catalyst, 300 psig pressure, and a flow rate of ethanol of 0.2 ml/min. For all examples, selectivity to 1-butanol is calculated as:

$$\text{butanol selectivity} = \frac{n_{BuOH}}{n_{0,EtOH} - n_{EtOH} - n_{ACH} - n_{BA}}$$

Where $n_{BuOH}$ is the molar flow rate of 1-butanol out of the reactor, $n_{0,\ EtOH}$ is the molar feed rate of ethanol into the reactor, $n_{EtOH}$ is the molar flow rate of ethanol out of the reactor, $n_{ACH}$ is the molar flow rate of acetaldehyde out of the reactor, and $n_{BA}$ is the molar flow rate of butyraldehyde out of the reactor (acetaldehyde and butyraldehyde are intermediates in the reaction chemistry from ethanol to 1-butanol). The $C_4$-$C_{12}$ alcohol selectivity is calculated as:

$$\text{C4-C12 alcohol selectivity} = \frac{n_{BuOH} + n_{C5-C12}}{n_{0,EtOH} - n_{EtOH} - n_{ACH} - n_{BA}}$$

Where $n_{BuOH}$, $n_{0,\ EtOH}$, $n_{EtOH}$, $n_{ACH}$, and $n_{BA}$ are the same as described above and $n_{C5-C12}$ is the total molar flow rate of all alcohols with 5 to 12 carbons.

TABLE 1

| Conversion and selectivity for ethanol to butanol and higher alcohols over catalyst | | | |
|---|---|---|---|
| Temp (° C.) | Ethanol Conversion (%) | Butanol Selectivity (%) | C4-C12 alcohol selectivity (%) |
| 220 | 6 | 75 | 96 |
| 230 | 8 | 65 | 96 |
| 240 | 10 | 72 | 96 |
| 250 | 12 | 69 | 96 |
| 260 | 14 | 73 | 96 |
| 270 | 13 | 77 | 96 |
| 280 | 17 | 76 | 95 |

Example 2

Catalyst Example 2

10 g of synthetic hydrotalcite were mixed with 1 g Mg-acetate tetrahydrate dissolved in ~15-20 ml water to form a slurry. Ethanol was added in small portions until all hydrotalcite particles were wetted by the aqueous phase. The slurry was mixed very well, dried at 105° C. followed by heating to 475° C. at a heating rate of 1° C./min and held at 475° C. for 2 hours followed by cooling to room temperature. A 5.5 g sample from the resulting powder was mixed into a wet paste with ~15 ml aqueous solution of 0.1004 g $Pd(NO_3)_2 \cdot 6H_2O$. The paste was dried at 105° C. The dry powder was heated to 475° C. at 1° C./min. and held at 475° C. for 2 hours then cooled down.

Figure 9:
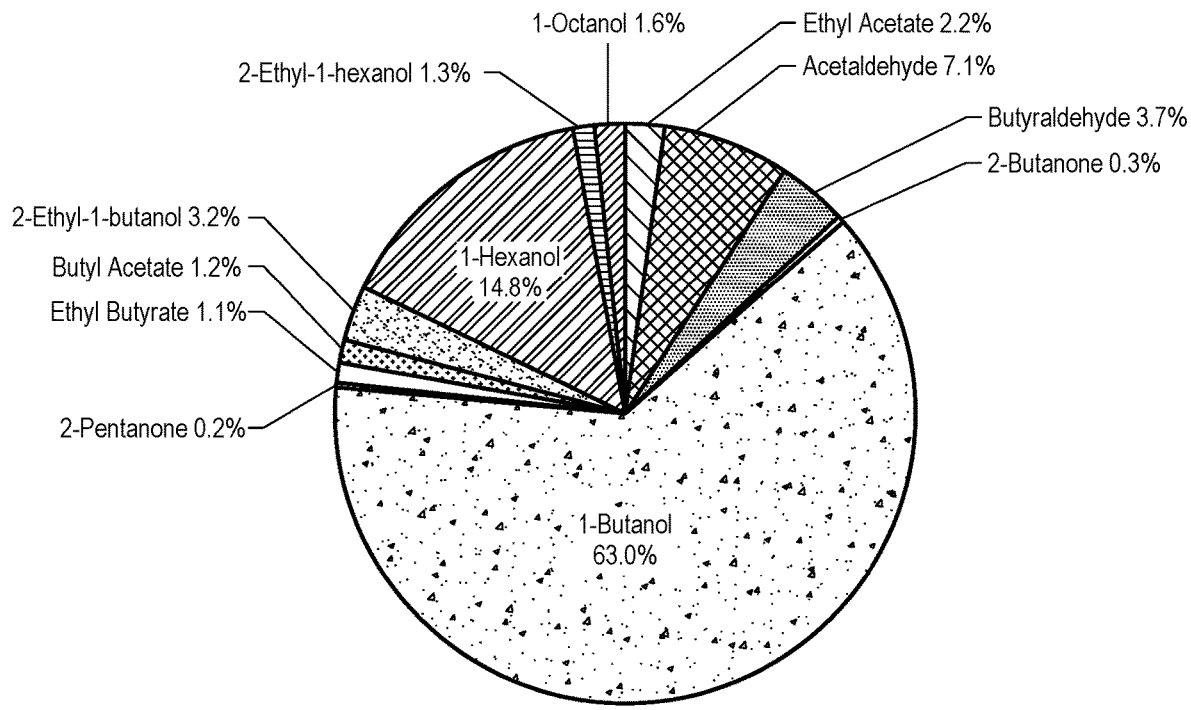
FIG. 9 illustrates another product distribution obtained by reacting ethanol over another embodiment of the catalyst.

The resulting catalyst powder was pressed in pellets, broken down to uniform sizes and subjected to testing for ethanol to n-butanol and higher alcohols conversion. The testing used 4.3 g of the catalyst at 260° C. and 300 psig pressure, with a flow rate of ethanol of 0.2 ml/min. The product distribution achieved is shown in FIG. 9 with an ethanol conversion of 20.2%. Table 2 shows the ethanol conversion and selectivity to both 1-butanol and to all alcohols in the C4-C12 range at different temperatures and at testing conditions using 4.3 g of the catalyst, 300 psig pressure, and a flow rate of ethanol of 0.2 ml/min.

TABLE 2

| Conversion and selectivity for ethanol to butanol and higher alcohols over catalyst | | | |
|---|---|---|---|
| Temp (° C.) | Ethanol Conversion (%) | Butanol Selectivity (%) | C4-C12 alcohol selectivity (%) |
| 220 | 8 | 86 | 97 |
| 230 | 10 | 78 | 94 |
| 240 | 13 | 76 | 94 |
| 250 | 17 | 69 | 95 |
| 260 | 20 | 69 | 95 |

Example 3

Catalyst Example 3

10 g of synthetic hydrotalcite were mixed with 4 g Ca-acetate hydrate dissolved in ~15-20 ml water to form a slurry. Ethanol was added in small portions until all hydrotalcite particles were wetted by the aqueous phase. The slurry was mixed very well, dried at 105° C. followed by heating to 475° C. at 1° C./min., and held at 475° C. for 2 hours followed by cooling to room temperature. A 5.5 g sample from the resulting powder was mixed into a wet paste with ~15 ml aqueous solution of 0.1210 g Pd(NO$_3$)$_2$.6H$_2$O. The paste was dried at 105° C. The dry powder was heated to 475° C. at a heating rate of 1° C./min, and held at 475° C. for 2 hours then cooled down.

Figure 10:
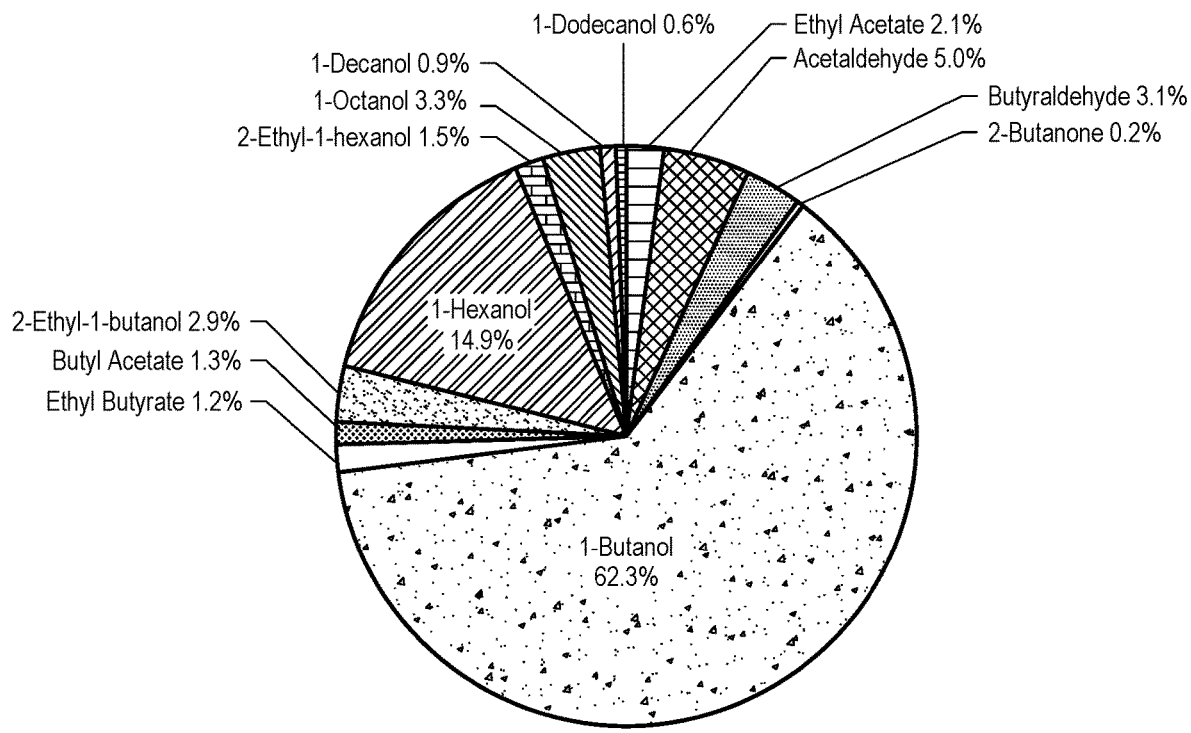
FIG. 10 illustrates another product distribution obtained by reacting ethanol over yet another embodiment of the catalyst.

The resulting catalyst powder was pressed in pellets, broken down to uniform sizes and subjected to testing for ethanol to n-butanol and higher alcohols conversion. The testing used 4.5 g of the catalyst at 260° C. and 300 psig pressure, with a flow rate of ethanol of 0.2 ml/min. The product distribution achieved is shown in FIG. 10 with an ethanol conversion of 26.2%. Table 3 shows the ethanol conversion and selectivity to both 1-butanol and to all alcohols in the C$_4$-C$_{12}$ range at different temperatures and at testing conditions using 4.5 g of the catalyst, 300 psig pressure, and a flow rate of ethanol of 0.2 ml/min.

TABLE 3

Conversion and selectivity for ethanol to butanol and higher alcohols over catalyst.

| Temp (° C.) | Ethanol Conversion (%) | Butanol Selectivity (%) | C4-C12 alcohol selectivity (%) |
|---|---|---|---|
| 220 | 15 | 54 | 95 |
| 230 | 18 | 55 | 95 |
| 240 | 19 | 65 | 95 |
| 250 | 23 | 65 | 95 |
| 260 | 26 | 65 | 95 |

Example 4

Catalyst Example 4

10 g synthetic hydrotalcite were heated to 475° C. at a heating rate of 1° C./min, and held at 475° C. for 2 hours followed by cooling to room temperature. A 5.5 g sample from the resulting powder was mixed into a wet paste with ~15 ml aqueous solution of 0.1072 g Pd(NO$_3$)$_2$.6H$_2$O. The paste was dried at 105° C. The dry powder was heated to 475° C. at a heating rate of 1° C./min, and held at 475° C. for 2 hours then cooled down.

Figure 11:
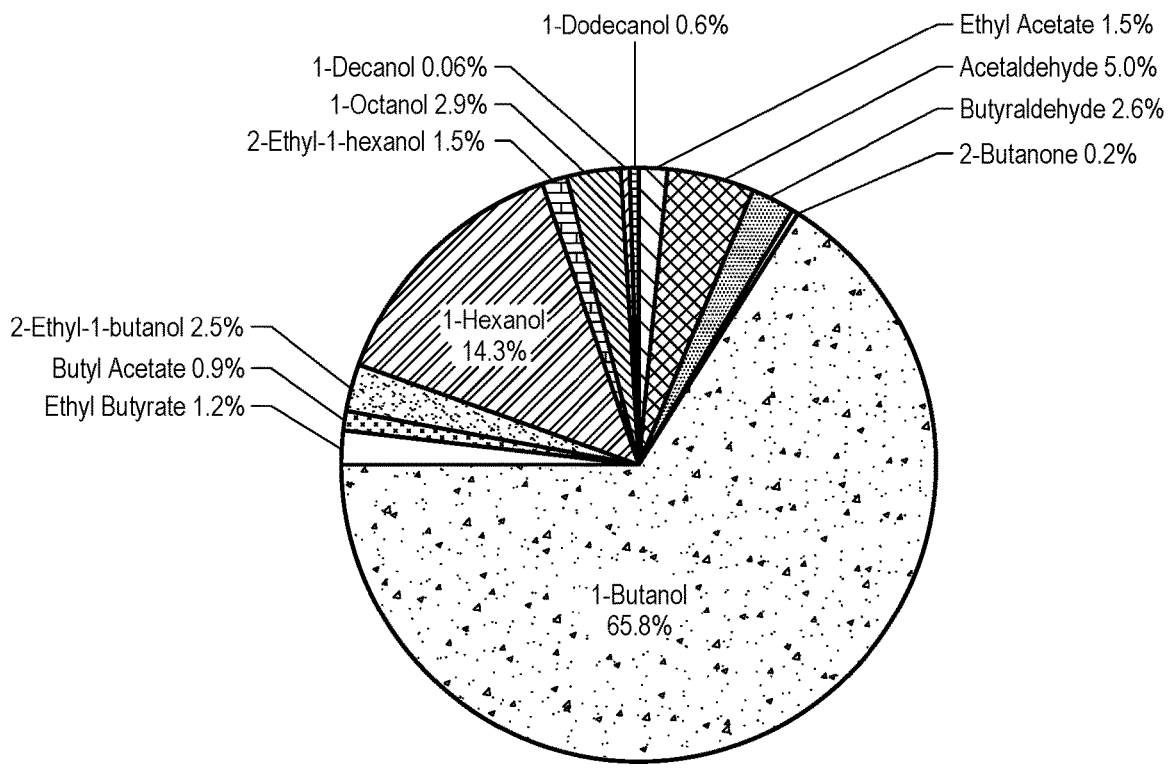
FIG. 11 illustrates another product distribution obtained by reacting ethanol over still another embodiment of the catalyst.

The resulting catalyst powder was pressed in pellets, broken down to uniform sizes and subjected to testing for ethanol to n-butanol and higher alcohols conversion. The testing used 5.0 g of the catalyst at 260° C. and 300 psig pressure, with a flow rate of ethanol of 0.2 ml/min. The product distribution achieved is shown in FIG. 11 with ethanol conversion of 25.0%. Table 4 shows the ethanol conversion and selectivity to both 1-butanol and to all alcohols in the C4-C12 range at different temperatures and at testing conditions using 5.0 g of the catalyst, 300 psig pressure, and a flow rate of ethanol of 0.2 ml/min.

TABLE 4

Conversion and selectivity for ethanol to butanol and higher alcohols over catalyst.

| Temp (° C.) | Ethanol Conversion (%) | Butanol Selectivity (%) | C4-C12 alcohol selectivity (%) |
|---|---|---|---|
| 220 | 13 | 75 | 98 |
| 230 | 16 | 71 | 96 |
| 240 | 21 | 66 | 96 |
| 250 | 23 | 69 | 96 |
| 260 | 25 | 69 | 96 |

Example 5

Catalyst Example 5

Figure 12:
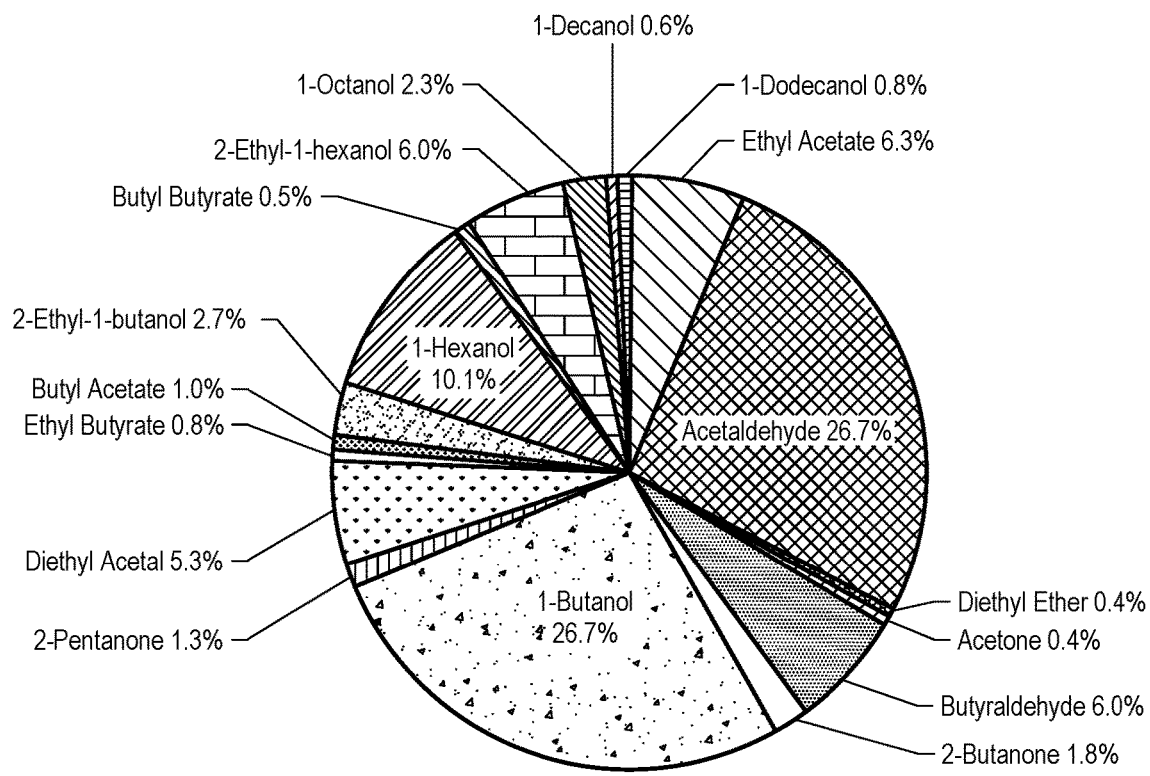
FIG. 12 illustrates another product distribution obtained by reacting ethanol over another embodiment of the catalyst.

10 g synthetic hydrotalcite were heated to 475° C. at a heating rate of 1° C./min. and held at 475° C. for 2 hours followed by cooling to room temperature. The resulting catalyst powder was pressed in pellets, broken down to uniform sizes. 0.37 g of Cu(NO$_3$)$_2$.2.5H$_2$O was dissolved in 10 ml of water and added to 10 g of silica support pellets (Saint Gobain SS61138). The silica pellets were then dried at 110° C., and then heated to 450° C. at a heating rate of 1° C./min and held at 450° C. for 2 hours before cooling to room temperature. The resulting catalyst pellets were then crushed to uniform sized (at approximately the same size as the final hydrotalcite catalyst). A physical mixture of the two catalysts was prepared by mixing 1 g of the Cu/SiO$_2$ catalyst with 5 g of hydrotalcite. This mixture was then tested in an ethanol to n-butanol (and higher alcohols) reaction at 260° C. and 300 psig pressure, with a flow rate of ethanol of 0.2 ml/min. The product distribution achieved is shown in FIG. 12 with ethanol conversion of 13.1%. Table 5 shows the ethanol conversion and selectivity to both 1-butanol and to all alcohols in the C$_4$-C$_{12}$ range at different temperatures and at testing conditions using 6.0 g of the catalyst (total), 300 psig pressure, and a flow rate of ethanol of 0.2 ml/min.

TABLE 5

Conversion and selectivity for ethanol to butanol and higher alcohols over catalyst.

| Temp (° C.) | Ethanol Conversion (%) | Butanol Selectivity (%) | C4-C12 alcohol selectivity (%) |
|---|---|---|---|
| 220 | 6 | 68 | 88 |
| 230 | 7 | 74 | 87 |
| 240 | 7 | 64 | 80 |
| 250 | 10 | 68 | 79 |
| 260 | 13 | 42 | 82 |
| 270 | 14 | 61 | 77 |
| 280 | 15 | 59 | 75 |

Example 6

Catalyst Example 6

250 g of synthetic hydrotalcite were heated to 475° C. at a heating rate of 1° C./min and held at 475° C. for 2 hours followed by cooling to room temperature. A 200 g sample from the resulting powder was mixed into a thick paste with 200 ml of an aqueous solution of 3.64 g Pd(NO$_3$)$_2$.6H$_2$O. The paste was extruded in a single screw extruder into ⅛ inch diameter trilobes. The resulting extrudates were dried at 105° C., and then heated to 475° C. at a heating rate of 1° C./min, held at 475° C. for 2 hours, and then cooled down.

Figure 13:
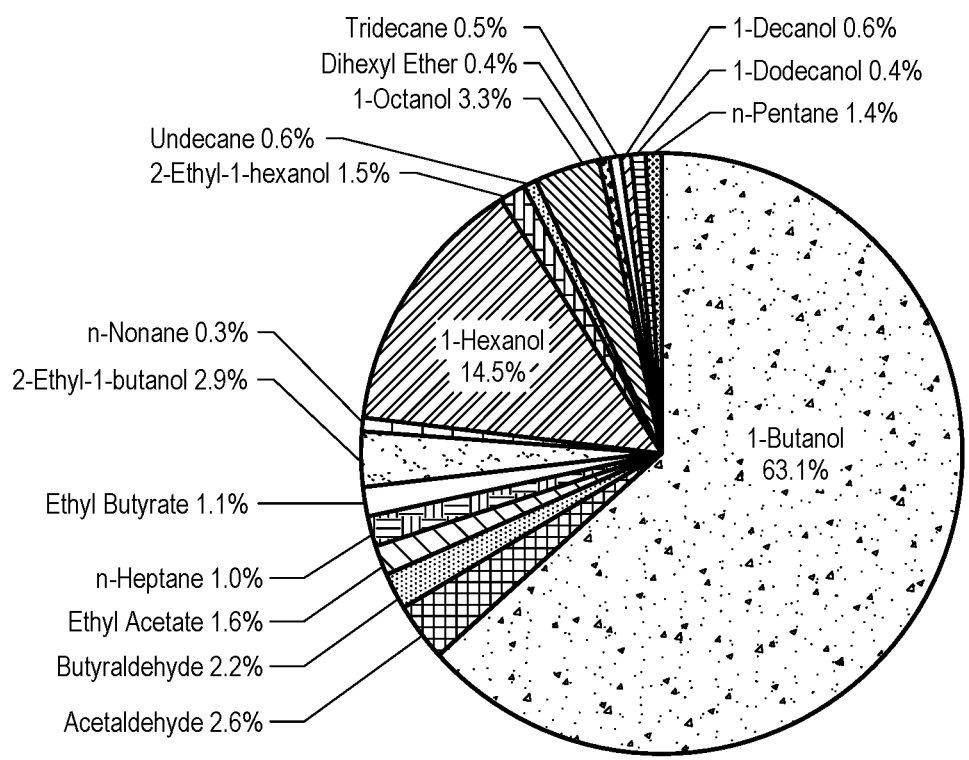
FIG. 13 illustrates another product distribution obtained by reacting ethanol over yet another embodiment of the catalyst.

The resulting catalyst pellets were broken down to uniform sizes and subjected to testing for ethanol to n-butanol and higher alcohols conversion. The testing used 5.0 g of the catalyst at 260° C. and 300 psig pressure, with a flow rate of ethanol of 0.173 ml/min. The product distribution achieved is shown in FIG. 13 with ethanol conversion of 27.6%. Table 4 shows the ethanol conversion and selectivity to both 1-butanol and to all alcohols in the C4-C12 range at different temperatures and at testing conditions using 5.0 g of the catalyst, 300 psig pressure, and a flow rate of ethanol of 0.173 ml/min.

TABLE 6

Conversion and selectivity for ethanol to butanol
and higher alcohols over catalyst example 6.

| Temp (° C.) | Ethanol Conversion (%) | Butanol Selectivity (%) | C4-C12 alcohol selectivity (%) |
|---|---|---|---|
| 220 | 13 | 62 | 91 |
| 230 | 17 | 58 | 91 |
| 240 | 21 | 63 | 91 |
| 250 | 24 | 63 | 90 |
| 260 | 28 | 64 | 90 |

Example 7

Catalyst Characterizations a Brunauer-Emmett-Teller (BET) analysis was performed on the catalyst examples prepared as described above. The BET results as shown in table 7 illustrate that the thermal decomposition of the hydrotalcite starting material increases both the surface area and pore volume of the material. The higher surface area may allow for better dispersion of the Pd metal on the hydrotalcite support.

TABLE 7

BET specific surface area and pore volume results for
catalyst examples 1-4 and the starting hydrotalcite.

| Sample | Surface Area (m²/g) | Pore Volume (cm³/g) |
|---|---|---|
| Synthetic Hydrotalcite | 8.5 | 0.0420 |
| Catalyst Example 1 | 25.2 | 0.0950 |
| Catalyst Example 2 | 69.6 | 0.2828 |
| Catalyst Example 3 | 50.8 | 0.1800 |
| Catalyst Example 4 | 54.2 | 0.3009 |

Figure 14:
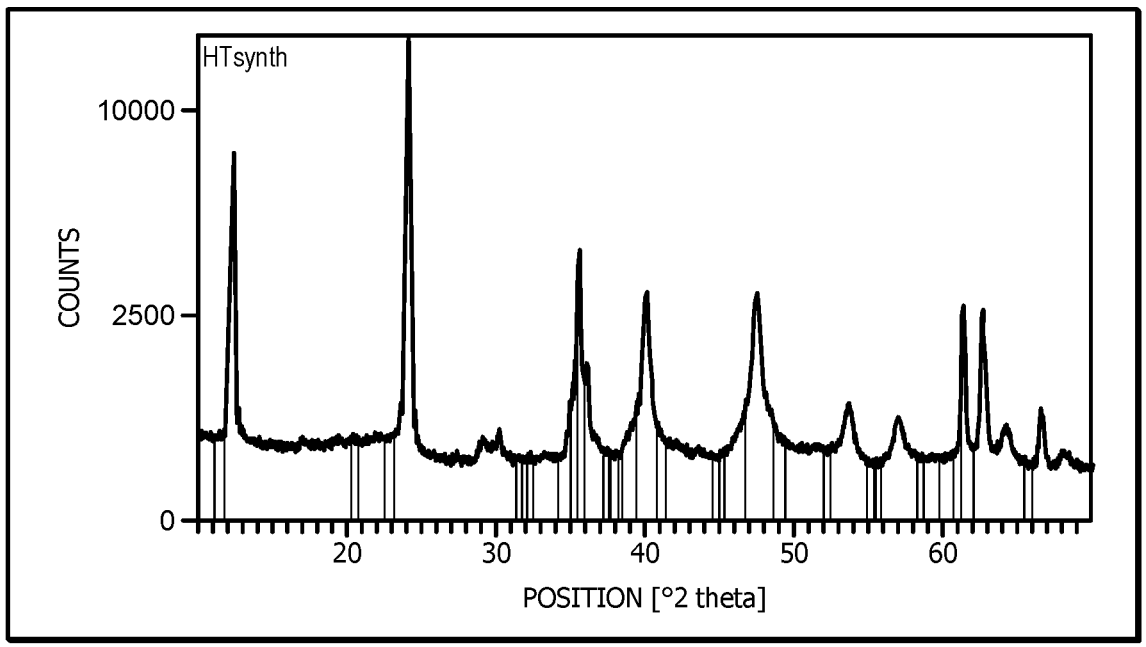
FIG. 14 illustrates an X-ray diffraction pattern of a hydrotalcite.
Figure 15:
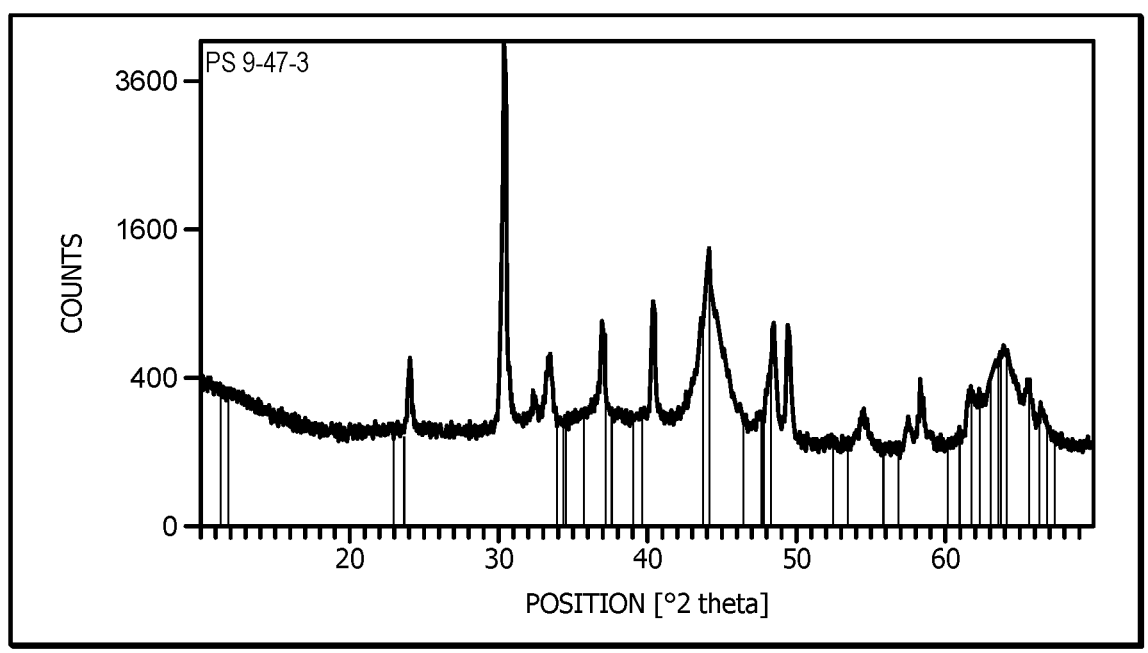
FIG. 15 illustrates an X-ray diffraction pattern of a sample of an embodiment of the catalyst.

The X-Ray Diffraction (XRD) pattern of the starting hydrotalcite material is shown in FIG. 14, and the XRD pattern of the final catalyst (Pd on decomposed hydrotalcite) is shown in FIG. 15 (illustrating the XRD pattern for the catalyst in example 3). The peaks in FIG. 15 correspond to the structure of meixnerite, which is a compound with the general structure of $Mg_6Al_2(OH)_{18} \cdot 4H_2O$. The XRD patterns for all of the catalyst examples are expected to be similar from the one presented in FIG. 15.

The XRD pattern of the synthetic hydrotalcite shows all of the typical reflections normally seen in hydrotalcite. The XRD pattern of the prepared catalyst in FIG. 15 shows that the double layered hydroxide structure of the hydrotalcite does not remain after the thermal treatment and Pd impregnation. The thermal decomposition and crystal structure changes of hydrotalcite are well documented. Upon heating hydrotalcite decomposes gradually through amorphous mixture of aluminum and magnesium oxides which at higher temperature become meixnerite ($Mg_6Al_2(OH)_{18} \cdot 4H_2O$). This is the reason for the change in the powder XRD pattern as well as the increase in the specific surface area (SSA) and pore volume as observed by BET method of nitrogen adsorption.

Having described numerous systems and methods herein, various embodiments of can include, but are not limited to:

In a first embodiment, a method of producing a catalyst comprises: heating a material comprising hydrotalcite, hydrocalumite, or both above a decomposition temperature; forming a decomposed material in response to the heating, wherein the decomposed material comprises a decomposed hydrotalcite, a decomposed hydrocalumite, or a combination of both; combining the decomposed material with a metal salt to form a catalyst mixture; and heating the catalyst mixture to convert the metal salt to a metal oxide, wherein the resulting metal oxide combined with the decomposed material forms the catalyst.

A second embodiment can include the method of the first embodiment, wherein the process further comprises: mixing a second metal salt with the material prior to heating the material.

A third embodiment can include the method of the first or second embodiment, wherein combining the decomposed material with a metal salt comprises mixing an aqueous solution of the metal salt with the decomposed material to form the catalyst mixture.

A fourth embodiment can include the method of any of the first to third embodiments, wherein the metal salt comprises one or more metals selected from the group consisting of: Pd, Cu, Pt, Cr, Ni, Fe, Ru, Rh, and Co.

A fifth embodiment can include the method of any of the first to fourth embodiments, wherein the second metal salt comprises an alkaline salt, an alkaline earth salt, or any combination thereof.

A sixth embodiment can include the method of any of the first to fifth embodiments, wherein the catalyst has a surface of between about 20 m²/g to about 100 m²/g.

A seventh embodiment can include the method of any of the first to sixth embodiments, wherein the catalyst has a pore volume of between about 0.05 cm³/g and about 0.4 cm³/g.

An eighth embodiment can include the method of any of the first to seventh embodiments, wherein the process further comprises combining the catalyst with a support material.

A ninth embodiment can include the method of any of the first to eight embodiments, further comprising: extruding the decomposed material into a granule prior to combining the decomposed material with the metal salt to form the catalyst mixture.

A tenth embodiment can include the method of any of the first to eight embodiments, further comprising: extruding the catalyst mixture into a granule.

In an eleventh embodiment, a catalyst for converting an alpha hydrogen alcohol to a higher alcohol can comprise a catalyst made according to a method of any of the first to tenth embodiments.

In a twelfth embodiment, a catalyst comprises: a first material having a formula:

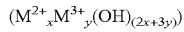

wherein the $M^{2+}$ ions comprise one or more of Mg, Ni, Pt, Pd, Zn, Co, Fe, or Cu, wherein the $M^{3+}$ ions comprise at least one of Al, Fe, or Cr, wherein x is in the range of from 2 to 7, wherein y is in the range of from 1.5 to 2.5; and one or more second materials comprising at least one of Pt, Pd, Cu, $Cr_2O_3$, $CuCr_2O_5$, Ni, Fe, Ru, Rh, Ir, Os, or Co.

A thirteenth embodiment can include the catalyst of the twelfth embodiment, wherein the catalyst has a surface of between about 20 m²/g to about 100 m²/g.

A fourteenth embodiment can include the catalyst of the twelfth or thirteenth embodiment, wherein the catalyst has a pore volume of between about 0.05 cm³/g and about 0.4 cm³/g.

A fifteenth embodiment can include the catalyst of any of the twelfth to fourteenth embodiments, wherein the first material comprises meixnerite ($Mg_6Al_2(OH)_{18} \cdot 4H_2O$).

A sixteenth embodiment can include the catalyst of any of the twelfth to fifteenth embodiments, wherein the one or more second materials comprise Pd.

A seventeenth embodiment can include the catalyst of any of the twelfth to sixteenth embodiments, wherein the one or more second materials comprise Cu.

An eighteenth embodiment can include the catalyst of any of the twelfth to seventeenth embodiments, where the loading of the one or more second materials is between about 0.01 wt % and about 5 wt. %

In a nineteenth embodiment, a catalyst comprises: a first material having a formula:

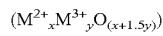

$(M^{2+}_x M^{3+}_y O_{(x+1.5y)})$ wherein the $M^{2+}$ ions comprise one or more of Mg, Ni, Pt, Pd, Zn, Co, Fe, or Cu, wherein the $M^{3+}$ ions comprise at least one of Al, Fe, or Cr, wherein x is in the range of from 0.5 to 1.5, wherein y is in the range of from 1.5 to 4; and one or more second materials comprising at least one of Pt, Pd, Cu, Cr2O3, Ni, Fe, Ru, Rh, Ir, or Co.

A twentieth embodiment can include the catalyst of the nineteenth embodiment, wherein the catalyst has a surface of between about 20 $m^2/g$ to about 100 $m^2/g$.

A twenty first embodiment can include the catalyst of the nineteenth or twentieth embodiment, wherein the catalyst has a pore volume of between about 0.05 $cm^3/g$ and about 0.4 $cm^3/g$.

A twenty second embodiment can include the catalyst of any of the nineteenth to twenty first embodiments, wherein the first material comprises a magnesium aluminum spinel ($MgAl_2O_4$).

A twenty third embodiment can include the catalyst of any of the nineteenth to twenty second embodiments, wherein the one or more second materials comprise Pd.

A twenty fourth embodiment can include the catalyst of any of the nineteenth to twenty third embodiments, wherein the one or more second materials comprise Cu.

A twenty fifth embodiment can include the catalyst of any of the nineteenth to twenty fourth embodiments, wherein the loading of the one or more second materials is between about 0.01 wt % and about 5 wt. %.

In a twenty sixth embodiment, a method for producing a higher alcohol comprises: contacting a reactant comprising ethanol with a catalyst at a reaction temperature and pressure sufficient to produce a reaction product, wherein the catalyst comprises a decomposed hydrotalcite mixed with one or more metal oxides, wherein the reaction product comprises a higher alcohol.

A twenty seventh embodiment can include the method of the twenty sixth embodiment, wherein the higher alcohol is butanol.

A twenty eighth embodiment can include the method of the twenty sixth embodiment, wherein the higher alcohol comprises a $C_4$-$C_{13}$ alcohol.

A twenty ninth embodiment can include the method of any of the twenty sixth to twenty eighth embodiments, wherein a conversion of ethanol to the higher alcohol is at least about 10%.

A thirtieth embodiment can include the method of any of the twenty sixth to twenty ninth embodiments, wherein a selectivity of the conversion of ethanol to the higher alcohol is at least about 90%.

A thirty first embodiment can include the method of any of the twenty sixth to thirtieth embodiments, wherein the one or more metal oxides comprise one or more metals selected from the group consisting of: Pd, Cu, Pt, Cr, Ni, Fe, Ru, Rh, and Co.

A thirty second embodiment can include the method of any of the twenty sixth to thirty first embodiments, wherein the one or more metal oxides comprises an alkaline salt, an alkaline earth salt, or any combination thereof.

A thirty third embodiment can include the method of any of the twenty sixth to thirty second embodiments, wherein the catalyst has a surface of between about 20 $m^2/g$ to about 100 $m^2/g$.

A thirty fourth embodiment can include the method of any of the twenty sixth to thirty third embodiments, wherein the catalyst has a pore volume of between about 0.05 $cm^3/g$ and about 0.4 $cm^3/g$.

A thirty fifth embodiment can include the method of any of the twenty sixth to thirty fourth embodiments, wherein the catalyst further comprises a support material.

In a thirty sixth embodiment, a reactive distillation method comprises: introducing a feed stream to a reactive distillation system, wherein the feed stream comprises one or more alpha hydrogen alcohols; contacting the feed stream with at least one catalyst in the reactive distillation column during a distillation, wherein the feed stream reacts in the presence of the at least one catalyst to produce a reaction product comprising one or more higher alcohols, wherein the catalyst comprises a material mixed with one or more metals, metal oxides, or a combination thereof, wherein the material comprises a decomposed hydrotalcite, a decomposed hydrocalumite, or a combination of both; and removing the higher alcohols during the distillation from the reactive distillation column as a bottoms stream.

A thirty seventh embodiment can include the method of the thirty sixth embodiment, wherein the one or more alpha hydrogen alcohols comprise one or more of ethanol, propanol, or butanol.

A thirty eighth embodiment can include the method of the thirty sixth or thirty seventh embodiment, wherein the one or more higher alcohols comprise a $C_6$-$C_{13}$ alcohol.

A thirty ninth embodiment can include the method of any of the thirty sixth or thirty eighth embodiments, wherein the one or more higher alcohols comprise at least one alcohol selected from the group consisting of: 1-hexanol, 2-ethyl-1-butanol, 1-octanol, 2-ethyl-2-hexanol, heptanol, decanol, and dodecanols.

A fortieth embodiment can include the method of any of the thirty sixth or thirty ninth embodiments, further comprising: converting at least a portion of the higher alcohols to one or more ethers.

A forty first embodiment, can include the method of any of the thirty sixth to fortieth embodiments, wherein the reactive distillation system comprises a reactive distillation column, and wherein contacting the feed stream with the at least one catalyst during the distillation comprises contacting the feed stream with the at least one catalyst in one or more side reactors in fluid communication with the reactive distillation column.

A forty second embodiment can include the method of the forty first embodiment, wherein the feed stream is introduced into the reactive distillation column.

A forty third embodiment can include the method of the forty first embodiment, wherein the feed stream is introduced into at least one of the one or more side reactors.

In the preceding discussion and in the claims, the terms "including" and "comprising" are used in an open-ended fashion, and thus should be interpreted to mean "including, but not limited to . . . ". At least one embodiment is disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting features of the embodiment(s) are also within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, Rl, and an upper limit, Ru, is disclosed, any number falling within the range is specifically disclosed. In particular, the following numbers within the range are specifically disclosed: $R=R_l+k*(R_u-R_l)$, wherein k is a variable ranging from 1 percent to 100 percent with a 1 percent increment, i.e., k is 1 percent, 2 percent, 3 percent, 4 percent, 5 percent, . . . , 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim means that the element is required, or alternatively, the element is not required, both alternatives being within the scope of the claim. Use of broader terms such as comprises, includes, and having should be understood to provide support for narrower terms such as consisting of, consisting essentially of, and comprised substantially of.

Accordingly, the scope of protection is not limited by the description set out above but is only limited by the claims which follow, that scope including all equivalents of the subject matter of the claims. Each and every claim is incorporated into the specification as an embodiment of the present disclosure. Thus, the claims are a further description and are an addition to the embodiments of the present disclosure. The discussion of a reference herein is not an admission that it is prior art to the present disclosure, especially any reference that may have a publication date after the priority date of this application. The disclosures of all patents, patent applications, and publications cited herein are hereby incorporated by reference, to the extent that they provide exemplary, procedural, or other details supplementary to those set forth herein.

What is claimed is:

1. A method for producing a higher alcohol comprising:
    contacting a reactant comprising ethanol with a catalyst at a reaction temperature and pressure sufficient to produce a reaction product,
    wherein the catalyst comprises: 1) a thermally decomposed hydrocalumite mixed with one or more metal oxides, or 2) a combination of a thermally decomposed hydrocalumite and a thermally decomposed hydrotalcite mixed with one or more metal oxides, wherein the reaction product comprises a higher alcohol.

2. The method of claim 1, wherein the higher alcohol is butanol.

3. The method of claim 1, wherein the higher alcohol comprises a $C_4$-$C_{13}$ alcohol.

4. The method of claim 1, wherein a conversion of ethanol to the higher alcohol is at least about 10%.

5. The method of claim 1, wherein a selectivity of the conversion of ethanol to the higher alcohol is at least about 90%.

6. The method of claim 1, wherein the one or more metal oxides comprise one or more metals selected from the group consisting of: Pd, Cu, Pt, Cr, Ni, Fe, Ru, Rh, and Co.

7. The method of claim 1, wherein the one or more metal oxides comprises an alkaline salt, an alkaline earth salt, or any combination thereof.

8. The method of claim 1, wherein the catalyst has a surface of between about 20 $m^2$/g to about 100 $m^2$/g.

9. The method of claim 1, wherein the catalyst has a pore volume of between about 0.05 $cm^3$/g and about 0.4 $cm^3$/g.

10. The method of claim 1, wherein the catalyst further comprises a support material.

11. A reactive distillation method comprising:
    introducing a feed stream to a reactive distillation system, wherein the feed stream comprises one or more alpha hydrogen alcohols;
    contacting the feed stream with at least one catalyst during a distillation, wherein the feed stream reacts in the presence of the at least one catalyst to produce a reaction product comprising one or more higher alcohols, wherein the catalyst comprises 1) a thermally decomposed hydrocalumite mixed with one or more metal oxides, or 2) a combination of a thermally decomposed hydrocalumite and a thermally decomposed hydrotalcite mized with one or more metal oxides; and
    removing the higher alcohols during the distillation from the reactive distillation system as a bottoms stream.

12. The method of claim 11, wherein the one or more alpha hydrogen alcohols comprise one or more of ethanol, propanol, or butanol.

13. The method of claim 11, wherein the one or more higher alcohols comprise a $C_6$-$C_{13}$ alcohol.

14. The method of claim 11, wherein the one or more higher alcohols comprise at least one alcohol selected from the group consisting of: 1-hexanol, 2-ethyl-1-butanol, 1-octanol, 2-ethyl-2-hexanol, heptanol, decanol, and dodecanols.

15. The method of claim 11, further comprising: converting at least a portion of the higher alcohols to one or more ethers.

16. The method of claim 11, wherein the reactive distillation system comprises a reactive distillation column, and wherein contacting the feed stream with the at least one catalyst during the distillation comprises contacting the feed stream with the at least one catalyst in one or more side reactors in fluid communication with the reactive distillation column.

17. The method of claim 16, wherein the feed stream is introduced into the reactive distillation column.

18. The method of claim 16, wherein the feed stream is introduced into at least one of the one or more side reactors.

19. The method of claim 1, wherein the catalyst comprises;
    a first material having a formula:

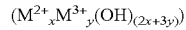

wherein the $M^{2+}$ ions comprise one or more of Mg, Ni, Pt, Pd, Zn, Co, Fe, or Cu, wherein the $M^{3+}$ ions comprise at least one of Al, Fe, or Cr, wherein x is in the range of from 2 to 7, wherein y is in the range of from 1.5 to 2.5; and
    one or more second materials comprising at least one of Pt, Pd, Cu, $Cr_2O_3$, $CuCr_2O_5$, Ni, Fe, Ru, Rh, Ir, Os, or Co.

20. The method of claim 19, wherein the first material comprises meixnerite ($Mg_6Al_2(OH)_{18} \cdot 4H_2O$).

21. The method of claim 1, wherein the catalyst comprises:
    a first material having a formula:

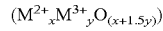

wherein the $M^{2+}$ ions comprise one or more of Mg, Ni, Pt, Pd, Zn, Co, Fe, or Cu, wherein the $M^{3+}$ ions comprise at least one of Al, Fe, or Cr, wherein x is in the range of from 0.5 to 1.5, wherein y is in the range of from 1.5 to 4; and one or more second materials comprising at least one of Pt, Pd, Cu, Cr2O3, Ni, Fe, Ru, Rh, Ir, or Co.

22. The method of claim 21, wherein the first material comprises a magnesium aluminum spinel ($MgAl_2O_4$).

23. The method of claim 1, wherein the one or more second materials comprise Pd.

24. The method of claim 1, wherein the one or more second materials comprise Cu.

25. The method of claim 1, where the loading of the one or more second materials is between about 0.01 wt % and about 5 wt. %.

26. The method of claim 11, wherein the catalyst comprises;

a first material having a formula:

$$(M^{2+}_xM^{3+}_y(OH)_{(2x+3y)})$$

wherein the $M^{2+}$ ions comprise one or more of Mg, Ni, Pt, Pd, Zn, Co, Fe, or Cu, wherein the $M^{3+}$ ions comprise at least one of Al, Fe, or Cr, wherein x is in the range of from 2 to 7, wherein y is in the range of from 1.5 to 2.5; and one or more second materials comprising at least one of Pt, Pd, Cu, $Cr_2O_3$, $CuCr_2O_5$, Ni, Fe, Ru, Rh, Ir, Os, or Co.

27. The method of claim 11, wherein the catalyst comprises:

a first material having a formula:

$$(M^{2+}_xM^{3+}_yO_{(x+1.5y)})$$

wherein the $M^{2+}$ ions comprise one or more of Mg, Ni, Pt, Pd, Zn, Co, Fe, or Cu, wherein the $M^{3+}$ ions comprise at least one of Al, Fe, or Cr, wherein x is in the range of from 0.5 to 1.5, wherein y is in the range of from 1.5 to 4; and one or more second materials comprising at least one of Pt, Pd, Cu, Cr2O3, Ni, Fe, Ru, Rh, Ir, or Co.

* * * * *